(12) United States Patent
Löfberg et al.

(10) Patent No.: US 8,258,107 B2
(45) Date of Patent: *Sep. 4, 2012

(54) IMMUNOSTIMULATORY METHOD

(75) Inventors: Robert Löfberg, Stockholm (SE); Oliver Von Stein, Upplands Väsby (SE)

(73) Assignee: Index Pharmaceuticals AB, Stockholm (SE)

( * ) Notice: Subject to any disclaimer, the term of this patent is extended or adjusted under 35 U.S.C. 154(b) by 600 days.

This patent is subject to a terminal disclaimer.

(21) Appl. No.: 11/917,482

(22) PCT Filed: Jun. 29, 2006

(86) PCT No.: PCT/SE2006/050229
§ 371 (c)(1),
(2), (4) Date: May 27, 2010

(87) PCT Pub. No.: WO2007/004977
PCT Pub. Date: Jan. 11, 2007

(65) Prior Publication Data
US 2010/0234449 A1    Sep. 16, 2010

Related U.S. Application Data

(60) Provisional application No. 60/696,173, filed on Jul. 1, 2005.

(51) Int. Cl.
*A01N 43/04*      (2006.01)
*C12P 19/34*      (2006.01)
*C12N 15/63*      (2006.01)
*C07H 21/02*      (2006.01)

(52) U.S. Cl. ............. 514/44; 435/91.1; 435/455; 514/1; 536/23.1

(58) Field of Classification Search ............. 435/6, 91.1, 435/455; 514/1, 2, 44; 536/23.1
See application file for complete search history.

(56) References Cited

U.S. PATENT DOCUMENTS

| | | |
|---|---|---|
| 5,366,878 A | 11/1994 | Pederson et al. |
| 5,591,840 A | 1/1997 | Narayanan et al. |
| 5,635,377 A | 6/1997 | Pederson et al. |
| 5,652,355 A | 7/1997 | Metelev et al. |
| 6,133,246 A | 10/2000 | McKay et al. |
| 6,143,881 A | 11/2000 | Metelev et al. |
| 6,214,806 B1 | 4/2001 | Krieg et al. |
| 6,218,371 B1 | 4/2001 | Krieg et al. |
| 6,239,116 B1 | 5/2001 | Krieg et al. |
| 6,294,382 B1 | 9/2001 | Bennett et al. |
| 6,339,068 B1 | 1/2002 | Krieg et al. |
| 6,346,614 B1 | 2/2002 | Metelev et al. |
| 6,406,705 B1 | 6/2002 | Davis et al. |
| 6,426,334 B1 | 7/2002 | Agrawal et al. |
| 6,426,336 B1 | 7/2002 | Carson et al. |
| 6,429,199 B1 | 8/2002 | Krieg et al. |
| 6,589,940 B1 | 7/2003 | Raz et al. |
| 6,653,292 B1 | 11/2003 | Krieg et al. |
| 6,943,240 B2 | 9/2005 | Bauer et al. |
| 6,949,520 B1 | 9/2005 | Hartmann et al. |
| 7,223,398 B1 | 5/2007 | Tuck et al. |
| 2002/0198165 A1 | 12/2002 | Bratzler et al. |
| 2003/0026801 A1 | 2/2003 | Weiner et al. |
| 2003/0050268 A1 | 3/2003 | Krieg et al. |
| 2003/0055014 A1 | 3/2003 | Bratzler |
| 2003/0078223 A1 | 4/2003 | Raz et al. |
| 2003/0087848 A1 | 5/2003 | Bratzler et al. |
| 2003/0166001 A1 | 9/2003 | Lipford et al. |
| 2003/0191079 A1 | 10/2003 | Krieg et al. |
| 2003/0212026 A1 | 11/2003 | Krieg et al. |
| 2003/0232074 A1 | 12/2003 | Lipford et al. ................. 424/450 |
| 2004/0030118 A1 | 2/2004 | Wagner et al. |
| 2004/0043023 A1 | 3/2004 | Vedeckis et al. |
| 2004/0131628 A1 | 7/2004 | Bratzler et al. |
| 2004/0234969 A1 | 11/2004 | Yuji et al. |
| 2004/0235770 A1 | 11/2004 | Davis et al. |
| 2004/0266719 A1 | 12/2004 | McCluskie et al. |
| 2005/0158325 A1 | 7/2005 | Hammerbeck et al. |
| 2005/0175630 A1 | 8/2005 | Raz et al. |
| 2005/0238660 A1 | 10/2005 | Babiuk et al. |
| 2006/0189550 A1 | 8/2006 | Jiang et al. |
| 2006/0211639 A1 | 9/2006 | Bratzler et al. |
| 2006/0229271 A1 | 10/2006 | Krieg et al. |
| 2006/0251677 A1 | 11/2006 | Bachmann et al. |
| 2006/0257851 A1 | 11/2006 | Bentwich |
| 2006/0287261 A1 | 12/2006 | Agrawal et al. |

(Continued)

FOREIGN PATENT DOCUMENTS

EP      0468520 A2     1/1992

(Continued)

OTHER PUBLICATIONS

Dean, et al., "Antisense oligonucleotide-based therapeutics for cancer", Oncogene, 2003, vol. 22, 9087-9096.
Musch et al, Aliment Pharmacol Ther, 16:1233-1239 (2002).
Simon et al, Allergy, 58:1250-1255 (2003).
Hawrylowicz et al, Nature Rev., 5:271-283 (2005).
Ikeda et al., Am. J. Resp Cell Mol Biol, 2003, 28:655-663.
Sun et al., Fundan Uni J Med Sci, 2003, 30(5):418-421.
Hartmann et al, J. Immunol, 2000, 164(2):944-952.
Aviles et al., Kidney Int, 2004, 66:60-67.
Chikanza et al, Rheumatology, 2004, 43:1337-1345.
Hauk et al., Am J Respir Cell Mol Biol., 2002, 27:361-7.
Leung et al, J Allergy Clin Immunol, 2003, 111(1):3-22.

(Continued)

*Primary Examiner* — Jane Zara
(74) *Attorney, Agent, or Firm* — Porter Wright Morris & Arthur

(57) ABSTRACT

The present invention makes it possible to enhance steroid efficacy in a steroid refractory or dependent patient afflicted with an inflammatory condition not responding or responding poorly or inadequately to anti-inflammatory treatment, by administering an oligonucleotide having the sequence 5 5'-Xm-CG-Yn-3' in an effective amount to said patient and wherein X is A, T, C or G, Y is A, T, C, or G, m=1-100, n=1-100 and wherein at least one CG dinucleotide is ummethylated. The invention also encompasses the use of said oligonucleotide for the manufacture of pharmaceuticals.

39 Claims, 10 Drawing Sheets

U.S. PATENT DOCUMENTS

| | | |
|---|---|---|
| 2009/0155307 A1 | 6/2009 | Davis et al. |
| 2009/0191188 A1 | 7/2009 | Krieg et al. |

FOREIGN PATENT DOCUMENTS

| | | |
|---|---|---|
| EP | 589330 A2 | 3/1994 |
| EP | 1078053 B1 | 9/2005 |
| EP | 0772619 B1 | 6/2006 |
| EP | 0948510 B1 | 7/2006 |
| EP | 1220684 B1 | 7/2006 |
| EP | 1077722 B1 | 8/2006 |
| EP | 1688147 A1 | 8/2006 |
| EP | 1700603 A2 | 9/2006 |
| EP | 1714969 A2 | 10/2006 |
| EP | 1746159 A2 | 1/2007 |
| EP | 1067956 B1 | 3/2007 |
| EP | 1296714 B1 | 8/2009 |
| EP | 1005368 B1 | 9/2009 |
| JP | 2008-535859 A | 9/2008 |
| WO | 96/02555 A1 | 2/1996 |
| WO | 97/28259 A1 | 8/1997 |
| WO | 97/47325 A1 | 12/1997 |
| WO | WO 97/47325 A1 | 12/1997 |
| WO | 98/16247 A1 | 4/1998 |
| WO | 98/37919 A | 9/1998 |
| WO | 99/56755 A | 11/1999 |
| WO | 99/58118 A | 11/1999 |
| WO | 99/62923 A | 12/1999 |
| WO | 00/06588 A1 | 2/2000 |
| WO | 01/22972 A2 | 4/2001 |
| WO | 01/22990 A2 | 4/2001 |
| WO | 01/68117 A2 | 9/2001 |
| WO | 01/97843 A1 | 12/2001 |
| WO | 02/22809 A2 | 3/2002 |
| WO | 02/053141 A1 | 7/2002 |
| WO | 02/085308 A2 | 10/2002 |
| WO | WO 02/085308 A2 | 10/2002 |
| WO | 2004/058159 A2 | 7/2004 |
| WO | 2004/058179 A2 | 7/2004 |
| WO | 2004/064782 A2 | 8/2004 |
| WO | 2004/087203 A2 | 10/2004 |
| WO | 2004/103301 A2 | 12/2004 |
| WO | 2005/080567 A1 | 9/2005 |
| WO | 2005/080568 A1 | 9/2005 |
| WO | 2005/081847 A2 | 9/2005 |
| WO | 2006/002038 A2 | 1/2006 |
| WO | 2006/015560 A1 | 2/2006 |
| WO | 2006/028742 A2 | 3/2006 |

OTHER PUBLICATIONS

Agrawal et al, Trends Mol Med., 2002, 8(3):114-21.
Bauer et al, J. Immunol, 2001, 166:5000-5007.
Jahn-Schmid et al., J. Allergy Clin. Immunol., 1999, 104(5):1015-1023.
Klinman et al., Vaccine, 1999, 17:19-25.
Krug et al., Eur. J. Immunol. 2001, 31:3026-3037.
Tighe et al., Eur. J. Immunol. 2000, 30:1939-1947.
Tokunaga et al., Mycrobiol. Immunol. 1992, 36(1):55-66.
Yamamoto et al., J Immunol. 1992, 148(12):4072-4076.

SEQUENCE LISTING

```
<160> NUMBER OF SEQ ID NOS: 10

<210> SEQ ID NO 1
<211> LENGTH: 19
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (1)..(19)

<400> SEQUENCE: 1
ggaacagttc gtccatggc                                               19

<210> SEQ ID NO 2
<211> LENGTH: 19
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (1)..(19)

<400> SEQUENCE: 2
ggaacagttg ctccatggc                                               19

<210> SEQ ID NO 3
<211> LENGTH: 19
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (1)..(19)

<400> SEQUENCE: 3
agctgagtag cctatagac                                               19

<210> SEQ ID NO 4
<211> LENGTH: 20
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (1)..(20)

<400> SEQUENCE: 4
ggtgcatcga tgcagggggg                                              20

<210> SEQ ID NO 5
<211> LENGTH: 24
<212> TYPE: DNA
<213> ORGANISM: Artificial Sequence
<220> FEATURE:
<223> OTHER INFORMATION: Oligonucleotide
```

```
<220> FEATURE:
<221> NAME/KEY: misc_feature
<222> LOCATION: (1)..(24)

<400> SEQUENCE: 5
tcgtcgtttt gtcgttttgt cgtt                                              24

<210> SEQ ID NO 6
<211> LENGTH: 24
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (1)..(24)

<400> SEQUENCE: 6
tgctgctttt gtgcttttgt gctt                                              24

<210> SEQ ID NO 7
<211> LENGTH: 19
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (1)..(19)

<400> SEQUENCE: 7
gaaacagatc gtccatggt                                                    19

<210> SEQ ID NO 8
<211> LENGTH: 19
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (1)..(19)

<400> SEQUENCE: 8
gaaacagatg ctccatggt                                                    19

<210> SEQ ID NO 9
<211> LENGTH: 20
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (1)..(20)

<400> SEQUENCE: 9
tccatgacgt tcctgacgtt                                                   20

<210> SEQ ID NO 10
<211> LENGTH: 20
<212> TYPE: DNA
<213> ORGANISM: Artificial Sequence
<220> FEATURE:
<223> OTHER INFORMATION: Oligonucleotide
```

```
<220> FEATURE:
<221> NAME/KEY: misc_feature
<222> LOCATION: (1)..(20)

<400> SEQUENCE: 10
tccatgagct tcctgagctt                                                    20
```

IMMUNOSTIMULATORY METHOD

CROSS REFERENCE TO RELATED APPLICATIONS

This application is a 35 USC §371 National Stage application of PCT Application No. PCT/SE2006/050229 filed Jun. 29, 2006; which claims the benefit under 35 USC §119(e) to U.S. Application Ser. No. 60/696,173 filed Jul. 1, 2005. The disclosure of each of the prior applications is considered part of and is incorporated by reference in the disclosure of this application.

FIELD OF THE INVENTION

The present invention relates to an immunostimulatory method. In particular, the present invention relates to a method wherein an oligonucleotide containing at least one unmethylated CG dinucleotides is administrated to a steroid refractory or dependent patient afflicted with an inflammatory condition.

BACKGROUND

Inflammation is a complex disease involving many factors and cell types. From a disease perspective, many years of research have taught us that inflammatory disorder such as asthma, rheumatoid arthritis, ulcerative colitis, and Cohn's disease and others have a distinct inflammatory cytokine profile. These profiles are the result of the nature of the responding lymphocytes. In other words, inflammation cannot be considered as just "inflammation" but rather different inflammatory diseases associated with different secreted cytokines that enhance the proliferation and differentiation of certain sub-populations of T helper cells.

The nature and magnitude of an immune response is largely dictated by the profile of the foreign antigen to which the immune system has been exposed. This event sets into motion a series of events that ultimately leads to the generation of humoral and cell-mediated immunity. These two different effector functions are brought about by the presence of two subpopulations of helper T cells (see FIG. 1). As also indicated, different inflammatory diseases can be segregated as being either Th1 or Th2, depending on the cytokine profile seen.

Under "normal" healthy conditions there is a delicate balance between pro-inflammatory cytokines typical of Th1 and anti-inflammatory cytokines typical of Th2. If this balance is lost, there will be a polarization resulting in predominantly Th1 or Th2 type inflammation and clinical manifestation of the disease will occur.

Some newer forms of therapeutics now attempt to restore the "in-balance" in for example Th1 type diseases by reducing the cytokine profile of Th1 and thereby allow more of a Th2 profile to occur (Neurath et al, 1995; Mannon et al, 2004). Over the last 5 years or so, many researchers have demonstrated both in vitro and in vivo the validity of the use of oligonucleotides as immunostimulatory agents in immunotherapy applications. The observation that phosphodiester and even modified phosphorothioate oligonucleotides can induce immune stimulation has created a growing interest in developing this effect as a therapeutic tool.

Bacterial DNA has immune stimulatory effects capable of activating B cells and natural killer cells, but vertebrate DNA does not (reviewed in Krieg, 1998. Applied Oligonucleotide Technology, C. A. Stein and A. M. Krieg, (Eds.), John Wiley and Sons, Inc., New York, N.Y., pp. 431-448). It is now understood that these immune stimulatory effects of bacterial DNA are a result of the presence of unmethylated CpG dinucleotides, in particular base contexts (CpG motifs), which are common in bacterial DNA, but methylated and underrepresented in vertebrate DNA (Krieg et al, 1995). The immune stimulatory effects of bacterial DNA can be mimicked with synthetic oligodeoxynucleotides (ODN) containing these CpG motifs. Such CpG ODN have highly stimulatory effects on human and murine leukocytes, inducing B cell proliferation; cytokine and immunoglobulin secretion; natural killer (NK) cell lytic activity and IFN-gamma secretion; and activation of dendritic cells (DCs) and other antigen presenting cells to express costimulatory molecules and secrete cytokines, especially the Th1-like cytokines that are important in promoting the development of Th1-like T cell responses. These immune stimulatory effects of native phosphodiester backbone CpG ODN are highly CpG specific in that the effects are dramatically reduced if the CpG motif is methylated, changed to a GpC, or otherwise eliminated or altered (Krieg et al, 1995 and Hartmann et al, 1999).

In early studies, it was thought that the immune stimulatory CpG motif followed the formula purine-purine-CpG-pyrimidine-pyrimidine (Krieg et al, 1995; Pisetsky, 1996 and Hacker et al., 1998).

Currently there is a significant amount of published data indicating that oligonucleotides containing CpG motifs induce certain cytokines, for example, human and mouse cells respond to CpG motif oligonucleotides by enhanced secretion of interferon-gamma (IFN-gamma) (Iho et al., 1999: Cowdery et al., 1996) IL-1, IL-6, TNF-alpha and IL-12 (Stacey et al., 1996; Jakob et al., 1998 and Sparwasser et al., 1998).

Due to the nature of cytokines induced, CpG containing oligonucleotides are largely considered to induce a Th1 profile both in vitro and in vivo (Zimmermann et al., 1998; Kline, 2000).

In addition to the presence of CpG motifs, researchers have also noted that synthesizing oligonucleotides with a full nuclease-resistant phosphorothioate (PS) backbone can potentate the stimulatory effects of the oligonucleotides, in that these oligonucleotides were much more potent at stimulating B cells, whereas the same sequence with native phosphodiester backbone had no effect (Zhao et al., 1996).

While the presence of a CpG motif within the sequence of an oligonucleotide can induce a strong Th1 cytokine response, this response should be considered in the overall context of the compounds state of chemical modification as well as the general sequence structure.

As already indicated in the background introduction to inflammation, there is a specific cytokine profile that becomes prominent in various types of inflammatory diseases. For example in asthmatic patients there are high levels of IL-4 and low levels of IFN-gamma. This cytokine picture would indicate that asthma is a Th2 type of disease. Rheumatoid arthritis by contrast is better associated with a Th1 type of inflammation characterized in that high levels of IFN-gamma and lower levels of IL-4 are seen.

The phenomenon of corticosteroid resistance has been most extensively studied in asthmatic patients and to a lesser degree in ulcerative colitis where evidence over the years has accumulated, pointing to a number of cytokine abnormalities. Both diseases are classified as Th2 type and interferons as well IL-10 have been implicated as being important factors in the pathogenesis of corticosteroid resistance.

It may be possible that immunostimulatory oligonucleotides that are able to induce endogenous production of such cytokines, such as interferons and IL-10, are able to influence the inflammatory status of steroid resistance or steroid dependent patients in a beneficial manner.

The evidence that certain cytokines can influence the steroid responsiveness is gathered from clinical studies conducted in corticosteroid resistant asthmatic and ulcerative colitis patients who were also all on corticosteroid therapies. In fact, this type of patient subgroup characteristic was the only common denominator between the clinical studies described below.

Interferons (IFNs) play crucial roles in the regulation of a wide variety of innate and adaptive immune responses. Type I interferons (IFN-alpha/beta) are central to the host defense against pathogens such as viruses, whereas type II interferon (IFN-gamma) mainly contributes to the T-cell-mediated regulation of the immune responses (Taniguchi and Takaoka, 2001). Interferons have also found their place in the successful treatment of various human diseases such as benign neoplastic (Gill et al, 1995) and viral diseases (Niederau et al, 1996; Zeuzem et al, 2000).

In a study (Simon et al, 2003), 10 patients with corticosteroid resistant asthma where administered IFN-alpha ($3\times10^6$ IU/day) (Roferon A® Roche) in addition to the prednisone dose they were all receiving. The trial demonstrated high efficacy in these patients and clinical signs of improvement occurring 1-2 weeks after cytokine therapy, allowing the dose of corticosteroids to be reduced. The authors further noted that the IFN-alpha treatment increased the capacity of peripheral blood T cells to produce IFN-gamma, suggesting there had been a shift from a Th2 type response (typical of asthma and allergic diseases) to a Th1 response.

Moreover, the authors showed that there was also an increase in blood T cells secreting IL-10, in those patients that had received cytokine therapy. As corticosteroids mediate their anti-inflammatory effects, in part, by increasing levels of IL-10, the authors conclude that administration of exogenous IFN-alpha broke the corticosteroid resistance in these patients.

Musch et al (2002) demonstrated a high response rate in corticosteroid refractory ulcerative colitis patients when given INF-beta i.v. The pilot study enrolled 25 severely ill ulcerative colitis patients proving refractory to basic medication. All patients where on corticosteroids at the time of cytokine treatment. Following treatment, 22 of the 25 (88%) went into remission within 3 weeks with a strong decrease in clinical activity index (CAI) noted 1 week after initiating treatment. The mean length of response was 13 months.

In another study, Sumer et al, (1995), reported an 82% improvement rate to s.c. IFN-alpha cytokine treatment in corticosteroid resistant ulcerative colitis patients. They further noted that the 23 patients responded to the cytokine therapy with a fast improvement (within 15 days) and were in complete clinical and endoscopic remission after 6 months of therapy. Three patients entered remission after longer therapy; however, all 26 patients were observed for more than 2 years without receiving additional therapy and remained in full clinical and endoscopic remission during this period.

Another cytokine that has received interest in the pathogenesis of corticosteroid resistance is IL-10. This cytokine is believed to have potent anti-inflammatory effects in that it can suppress the production of pro-inflammatory cytokines. It also has broad implications in the development of certain inflammatory diseases, most noticeably allergy and asthma (Hawrylowicz et al, 2005), as well as playing a central role in the regulation of immune responses. It is believed that corticosteroids exert their anti-inflammatory effects in part by enhancing IL-10 production (Richards et al, 2005).

Numerous clinical studies have indicated that there is a general lack of sufficient levels of IL-10 in asthmatics which may potentially contribute to a more intensive inflammation. In a randomized double-blind clinical study conducted in children with moderate atopic asthma, Stelmach et al (2002) demonstrated that treatment with Triamcinolone, a corticosteroid, and montelukast, an anti-leukotriene, significantly increased levels of IL-10 in blood serum and in addition significantly improved clinical symptoms.

In another clinical study, levels of IL-10 and IL-10 producing cells were shown to be significantly reduced in patients with severe persistent asthma when compared to mild asthma (Tomitai et al, 2002). These observations were in agreement with previous findings that there is a defect in the production of cells that are able to produce IL-10 in asthmatic subjects (Tormey et al, 1998).

This defect was also shown to exist in corticosteroid resistant asthmatic patients. Under normal conditions, corticosteroids will cause an increased production of IL-10 in corticosteroid sensitive patients. However, Hawrylowicz et al (2002) could confirm that in corticosteroid resistant asthmatic patients, corticosteroids failed to induce IL-10 synthesis. These observations suggest a strong link between induction of IL-10 synthesis and efficacy of corticosteroids.

In a recently published study (Xystrakis et al, 2006), the authors isolated PBMC from corticosteroid resistant asthmatic patients and could demonstrate that addition of vitamin D3 with dexamethasone to these cultures enhanced IL-10 synthesis to levels observed in cells from corticosteroid sensitive patients cultured with dexamethasone alone. Furthermore, and perhaps most significantly, pre-treatment with IL-10 fully restored IL-10 synthesis in these cells in response to dexamethasone.

The use of human bacterial flora to treat gastrointestinal (GI) disorders is not a novel concept, having been practiced periodically for more than 40 years (Eiseman et al, 1958). Significant clinical improvements have been observed in numerous GI disorders including inflammatory bowel disease (IBD) (Bennet and Brinkman 1989). Borody et al, reported in 2003 that human bacteriotherapy could be used to treat severe corticosteroid resistant ulcerative colitis (UC).

In a small study, 6 chronic UC patients who had all previously failed maximum tolerated standard corticosteroid therapies were all given a single faecal enema concomitant to corticosteroid therapies they were currently on. Complete reversal of UC was achieved in all 6 patients following the rectal infusion. The authors also state that all patients ceased anti-inflammatory therapy within 6 weeks and remained in remission in one case for up to 13 years. The apparent success of bacteriotherapy in resistant ulcerative colitis patients may be due to the repopulation of the colon with a "healthy" bacterial flora, but equally as the authors suggest, may also be due to the instillation of a large amount of bacterial DNA, containing abundant CpG motifs, which induced a beneficial immunomodulating effect resulting in complete reversal of the disease.

A study in asthmatic compared the response to a steroid (prednisone) in both steroid resistant and steroid sensitive patients. The patients were first given a "wash-out" period of one week before administration of the steroid. Cytokine profiles before administration and 1 week after indicated that those patients that responded to the steroid moved from a Th2 type to a more Th1 like status. By contrast, those patients that failed to respond to the administered steroid remained Th2 type (Naseer et al., 1997).

While the reason for steroid resistance in asthmatic patients is not entirely clear, numerous studies in humans have indicated that those patients that are resistant to steroids have high persistent levels of IL-2/4 that are not suppressed by the action of steroids. Furthermore, in vitro studies indicate that when IL-2/4 is placed in the culture medium, the cells become resistant to the action of steroids (Sousa A R et al., 2000; Hamid Q A et al., 1999).

In rheumatoid arthritis a similar scenario has been suggested in that steroid resistant patients demonstrate high levels of IL-4, which cannot be reduced when challenged with steroids (Chikanza et al., 2004). Of interest are the findings that INF-gamma is able to down regulate IL-4 responses (Eui-Young et al., 2000; Smeltz et al., 2002) at the level of transcription.

Steroid resistance or dependence is still a major clinical concern for a large number of patients afflicted with inflammatory diseases as current therapies rely on the use of potent immunomodulators that can induce serious side-effects. A simple straightforward method to enhance steroid efficacy in a steroid unresponsive individual with little risk of unwanted side-effects would essentially improve anti-inflammatory treatment, thus ameliorating the disease in question, and increasing the quality and length of life for a large number of patients.

SUMMARY OF THE INVENTION

The present invention relates to the surprising discovery of a method for enhancing steroid efficacy in a steroid refractory or steroid dependent patient afflicted with an inflammatory condition not responding or responding poorly or inadequately to anti-inflammatory treatment or there is an inability to wean the anti-inflammatory treatment dosing level down. An oligonucleotide having the sequence 5'-$X_m$-CG-$Y_n$-3' is administered in an effective amount to said patient. In the sequence of the oligonucleotide X is A, T, C or G, Y is A, T, C, or G, m=1-100, n=1-100 and at least one CG dinucleotide is unmethylated.

The present invention also relates to the use of the above mentioned oligonucleotides for the manufacture of a medicament for enhancing steroid efficacy in a steroid refractory patient afflicted with an inflammatory condition not responding or responding poorly or inadequately to anti-inflammatory treatment.

The attached set of claims is hereby incorporated in its entirety.

DETAILED DESCRIPTION

Figure 1:
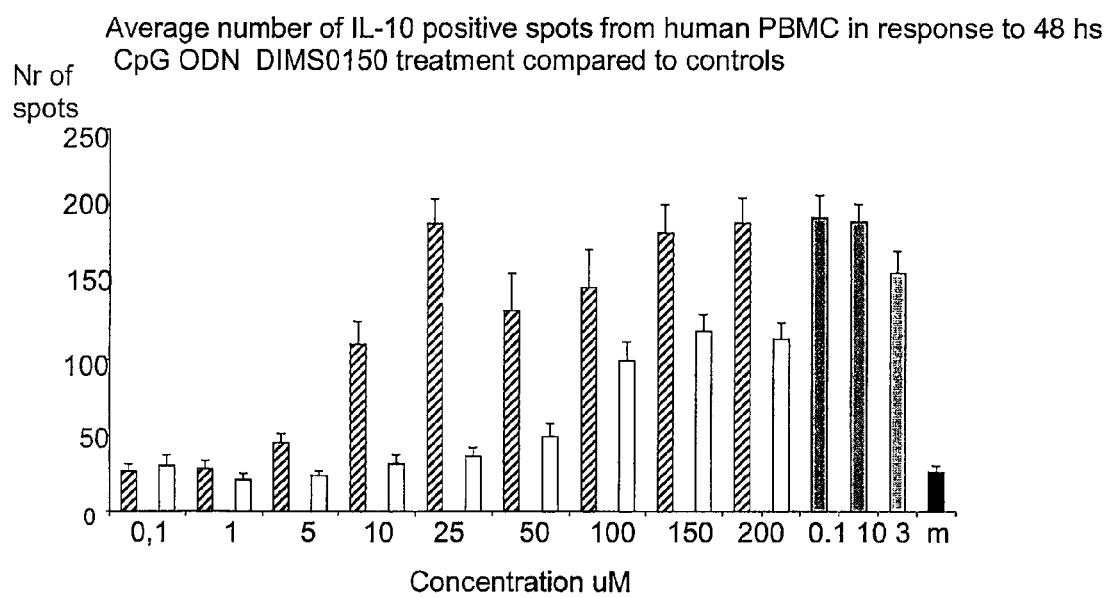
FIG. 1 is a graph showing the number of IL-10 producing cells in response to 48 hrs of DIMS0150 stimulation in PBMC from five (n=5) different healthy donors analysed by ELISpot. PBMC were incubated in medium (basal) or with increasing concentrations (0.1, 1, 5, 10, 25, 100, 150 or 200 μM) of the CpG containing DIMS0150 or, or its GpC control IDX0526, or the CpG ODNs, IDX0910 (0.1 or 10 μM) and IDX0900 (3 μM) for 48 hours before detection of IL-10 positive spots. Each bar of the histogram represents the average results from five different blood donors. Samples were performed and analysed in triplicate for each experiment/blood donor. Note that IDX0900 was tested on three individuals (n=3).

As used herein, the terms "steroid resistant" and "steroid refractory" refers to patients having inflammatory diseases in which administration of steroid treatment, typically effective in patients having such diseases, is ineffective. In this context "steroid resistant" and "steroid refractory" patients include, but are not limited to, patients who do not respond or respond poorly or inadequately as judged by common appropriate physiological parameters to systemic or topical administered steroids. Two types of steroid resistant patients have been described i.e. acquired steroid resistance (Type I) and primary steroid resistance (Type II), both of which are comprised in the present invention.

As used herein, the term "steroid dependence", refers to patients with the inability to be weaned off systemic or topical administered steroid treatment.

References describing immunostimulatory activity of polynucleotides include, but are not limited to, Krug et al. (2001); Bauer et al. (2001); Klinman et al. (1999); Jahn-Schmid et al. (1999) and Tighe et al. (2000).

Further references describing immunostimulatory sequences include: Tokunaga et al. (1992); Yamamoto et al. (1992) and EP 468,520; WO 96/02555; WO 97/28259; WO 98/16247; U.S. Pat. Nos. 6,339,068, 6,406,705, 6,426,334 and 6,426,336.

All patents, patent applications, and publications cited herein are hereby incorporated by reference in their entirety.

For purposes of the invention, the term "oligonucleotide" refers to a polynucleoside formed from a plurality of linked individual nucleoside units. Such oligonucleotides can be obtained from existing nucleic acid sources, including genomic or cDNA, but are preferably produced by synthetic methods. The nucleoside residues can be coupled to each other by any of the numerous known internucleoside linkages. Such internucleoside linkages include, without limitation, the natural internucleoside phosphodiester bond or indeed modified internucleosides such as, but not limited to, phosphorothioate, phosphorodithioate, alkylphosphonate, alkylphosphonothioate, phosphotriester, phosphoramidate, siloxane, carbonate, carboalkoxy, acetamidate, carbamate, morpholino, borano, thioether, bridged phosphoramidate, bridged methylene phosphonate, bridged phosphorothioate, and sulfone internucleoside linkages. The term "oligonucleotide" also encompasses polynucleosides having one or more stereospecific internucleoside linkage (e.g., (Rp)- or (Sp)-phosphorothioate, alkylphosphonate, or phosphotriester linkages). As used herein, the terms "oligonucleotide" and "dinucleotide" are expressly intended to include polynucleosides and dinucleosides having any such internucleoside linkage, whether or not the linkage comprises a phosphate group. In certain preferred embodiments, these internucleoside linkages may be phosphodiester, phosphorothioate, or phosphorodithioate linkages, or combinations thereof.

The term "oligonucleotide" also encompasses polynucleosides having additional substituents including, without limitation, protein groups, lipophilic groups, intercalating agents, diamines, folic acid, cholesterol and adamantane. The term "oligonucleotide" also encompasses any other nucleobase containing polymer, including, without limitation, peptide nucleic acids (PNA), peptide nucleic acids with phosphate groups (PHONA), locked nucleic acids (LNA), morpholino-backbone oligonucleotides, and oligonucleotides having backbone sections with alkyl linkers or amino linkers.

The oligonucleotides of the invention can include naturally occurring nucleosides, modified nucleosides, or mixtures thereof. As used herein, the term "modified nucleoside" is a nucleoside that includes a modified heterocyclic base, a modified sugar moiety, or a combination thereof. In some embodiments, the modified nucleoside is a non-natural pyrimidine or purine nucleoside, as herein described. In some embodiments, the modified nucleoside is a 2'-substituted ribonucleoside an arabinonucleoside or a 2'-deoxy-2'-substituted-arabinoside.

The term "oligonucleotide" includes hybrid and chimeric oligonucleotides. A "chimeric oligonucleotide" is an oligonucleotide having more than one type of internucleoside linkage within its sequence structure. One preferred example of such a chimeric oligonucleotide is a chimeric oligonucleotide comprising a phosphorothioate, phosphodiester or phosphorodithioate region and non-ionic linkages such as alkylphosphonate or alkylphosphonothioate linkages (Pederson et al. U.S. Pat. Nos. 5,635,377 and 5,366,878).

A "hybrid oligonucleotide" is an oligonucleotide having more than one type of nucleoside. One preferred example of such a hybrid oligonucleotide comprises a ribonucleotide or 2'-substituted ribonucleotide region, and a deoxyribonucleotide region (Metelev and Agrawal, U.S. Pat. Nos. 5,652,355, 6,346,614 and 6,143,881).

For purposes of the invention, the term "immunomodulatory oligonucleotide" refers to an oligonucleotide as described above that induces an immune response either stimulating the immune system or repressing the immune system or both in an organism when administered to a vertebrate, such as a mammal. As used herein, the term "mammal" includes, without limitation rats, mice, cats, dogs, horses, cattle, cows, pigs, rabbits, non-human primates, and humans.

Preferably, the immunomodulatory oligonucleotide comprises at least one naturally occurring phosphodiester, or one modified phosphorothioate, or phosphorodithioate internucleoside linkage, however preferred linkages or indeed backbone modifications including, without limitation, methylphosphonates, methyl phosphonothioates, phosphotriesters, phosphothiotriesters, phosphorothioates, phosphorodithioates, triester prodrugs, sulfones, sulfonamides, sulfamates, formacetal, N-methylhydroxylamine, carbonate, carbamate, morpholino, boranophosphonate, phosphoramidates, especially primary amino-phosphoramidates, N3 phosphoramidates and N5 phosphoramidates, and stereospecific linkages (e.g., (Rp)- or (Sp)-phosphorothioate, alkylphosphonate, or phosphotriester linkages).

The term "immunomodulatory response" describes the change of an immune response when challenged with an immunomodulatory oligonucleotide. This change is measurable often through the release of certain cytokines such as interferons as well as other physiological parameters such as proliferation. The response can equally be one that serves to stimulate the immune system as well as to repress the immune system depending on the cytokines induced by the immunomodulatory oligonucleotide in question.

In some embodiments, the immunomodulatory oligonucleotide comprises an immunostimulatory dinucleotide of formula 5'-Pyr-Pur-3', wherein Pyr is a natural or synthetic pyrimidine nucleoside and Pur is a natural or synthetic purine nucleoside. In some preferred embodiments, the immunomodulatory oligonucleotide comprises an immunostimulatory dinucleotide of formula 5'-Pur*-Pur-3', wherein Pur* is a synthetic purine nucleoside and Pur is a natural or synthetic purine nucleoside. In various places the dinucleotide is expressed as RpG, C*pG or YZ, in which case respectively, R, C*, or Y represents a synthetic purine. A particularly preferred synthetic purine is 2-oxo-7-deaza-8-methyl-purine. When this synthetic purine is in the Pur* position of the dinucleotide, species-specificity (sequence dependence) of the immunostimulatory effect is overcome and cytokine profile is improved. As used herein, the term "pyrimidine nucleoside" refers to a nucleoside wherein the base component of the nucleoside is a monocyclic nucleobase. Similarly, the term "purine nucleoside" refers to a nucleoside wherein the base component of the nucleoside is a bicyclic nucleobase. For purposes of the invention, a "synthetic" pyrimidine or purine nucleoside includes a non-naturally occurring pyrimidine or purine base, a non-naturally occurring sugar moiety, or a combination thereof.

In some embodiments, the sugar moiety of the nucleoside can be a non-naturally occurring sugar moiety. For purposes of the present invention, a "naturally occurring sugar moiety" is a sugar moiety that occurs naturally as part of a nucleic acid, e.g., ribose and 2'-deoxyribose, and a "non-naturally occurring sugar moiety" is any sugar that does not occur naturally as part of a nucleic acid, but which can be used in the backbone for an oligonucleotide, for example but mot limited to hexose. Arabinose and arabinose derivatives are examples of preferred sugar moieties.

Preferred immunostimulatory moieties according to the invention further include nucleosides having sugar modifications, including, without limitation, 2'-substituted pentose sugars including, without limitation, 2'-O-methylribose, 2'-O-methoxyethyl-ribose, 2'-O-propargylribose, and 2'-deoxy-2'-fluororibose; 3'-substituted pentose sugars, including, without limitation, 3'-O-methylribose; 1',2'-dideoxyribose; arabinose; substituted arabinose sugars, including, without limitation, 1'-methylarabinose, 3'-hydroxymethylarabinose, 4'-hydroxymethylarabinose, 3'-hydroxyarabinose and 2'-substituted arabinose sugars; hexose sugars, including, without limitation, 1,5-anhydrohexitol; and alpha-anomers.

In another embodiment, preferred immunostimulatory moieties according to the invention further include oligonucleotides having other carbohydrate backbone modifications and replacements, including peptide nucleic acids (PNA), peptide nucleic acids with phosphate groups (PHONA), locked nucleic acids (LNA), morpholino backbone oligonucleotides, and oligonucleotides having backbone linker sections having a length of from about 2 angstroms to about 200 angstroms, including without limitation, alkyl linkers or amino linkers. The alkyl linker may be branched or unbranched, substituted or unsubstituted, and chirally pure or a racemic mixture. Most preferably, such alkyl linkers have from about 2 to about 18 carbon atoms. In some preferred embodiments such alkyl linkers have from about 3 to about 9 carbon atoms. Some alkyl linkers include one or more functional groups selected from the group consisting of hydroxy, amino, thiol, thioether, ether, amide, thioamide, ester, urea, and thioether. Some functionalized alkyl linkers are poly(ethylene glycol) linkers of formula -0-(CH2-CH2-O—), (n=1-9). Some other functionalized alkyl linkers are peptides or amino acids.

In a further embodiment preferred immunostimulatory moieties according to the invention further include DNA isoforms, including, without limitation, -L-deoxyribonucleosides and a-deoxyribonucleosides. Preferred immunostimulatory moieties according to the invention incorporate 3' modifications, and further include nucleosides having unnatural internucleoside linkage positions, including, without limitation, 2'-5',2'-2',3'-3' and 5'-5' linkages.

The immunomodulatory oligonucleotide according to the invention comprise at least five nucleosides linked via internucleoside linkage or a functionalized nucleobase or sugar via a non-nucleotidic linker. For purposes of the invention, a "non-nucleotidic linker" is any moiety that can be linked to the oligonucleotides by way of covalent or non-covalent linkages.

Non-covalent linkages include, but are not limited to, electrostatic interaction, hydrophobic interactions, -stacking interactions, and hydrogen bonding. The term "non-nucleotidic linker" is not meant to refer to an internucleoside linkage, as described above, e.g. a phosphodiester, phosphorothioate, or phosphorodithioate functional group, that directly connects the 3'-hydroxyl groups of two nucleosides. For purposes of this invention, such a direct 3'-3' linkage (no linker involved) is considered to be a "nucleotidic linkage."

In some embodiments, the non-nucleotidic linker is a metal, including, without limitation, gold particles. In some other embodiments, the non-nucleotidic linker is a soluble or insoluble biodegradable polymer bead.

In yet other embodiments, the non-nucleotidic linker is an organic moiety having functional groups that permit attachment to the oligonucleotide. Such attachment preferably is by any stable covalent linkage.

In some embodiments, the non-nucleotidic linker is a biomolecule, including, without limitation, polypeptides, antibodies, lipids, antigens, allergens, and oligosaccharides. In some other embodiments, the non-nucleotidic linker is a small molecule. For purposes of the invention, a small molecule is an organic moiety having a molecular weight of less than 1,000 Da.

In some embodiments, the small molecule is an aliphatic or aromatic hydrocarbon, either of which optionally can include, either in the linear chain connecting the oligonucleotides or appended to it, one or more functional groups selected from the group consisting of hydroxy, amino, thiol, thioether, ether, amide, thioamide, ester, urea, and thiourea. The small molecule can be cyclic or acyclic. Examples of small molecule linkers include, but are not limited to, amino acids, carbohydrates, cyclodextrins, adamantane, cholesterol, haptens and antibiotics. However, for purposes of describing the non-nucleotidic linker, the term "small molecule" is not intended to include a nucleoside.

In some embodiments, the small molecule linker is glycerol or a glycerol homolog of the formula HO—(CH2)o-CH(OH)—(CH2)p-OH, wherein o and p independently are integers from 1 to about 6, from 1 to about 4, or from 1 to about 3. In some other embodiments, the small molecule linker is a derivative of 1,3-diamino-2-hydroxypropane. Some such derivatives have the formula HO—(CH2) m-C(O)NH—CH2—CH(OH)—CH2—NHC(O)-m-OH, wherein m is an integer from 0 to about 10, from 0 to about 6, from 2 to about 6, or from 2 to about 4.

Modified or substituted oligonucleotides are often preferred over native forms because of desirable properties such as, for example, enhanced cellular uptake, enhanced affinity for nucleic acid target and increased stability in the presence of nucleases. An oligonucleotide is usually comprised of more than two (2), and typically more than ten (10) and up to one hundred (100) or more deoxyribonucleotides or ribonucleotides, although preferably between about eight (8) and about forty (40), most preferably between about eight (8) and about twenty (20). The exact size will depend on many factors, which in turn depends on the ultimate function or use of the oligonucleotide. The oligonucleotide may be generated in any manner, including chemical synthesis, DNA replication, reverse transcription, or a combination thereof.

In the inventive method the oligonucleotides can be administered by any appropriate administration route, such as, but not limited to, inhalation, ophthalmic, intranasal, parenteral, oral, intradermal and rectal administration. If the patient is also on steroid treatment or other anti-inflammatory treatments such as the use of immunomodulators, the steroids and immunomodulators can be administered together with the oligonucleotides or separately. The route of administration of the oligonucleotides is independent of the route of administration of steroids.

The phrase "therapeutically effective amount" as used herein relates to an amount sufficient to enhance steroid efficacy to some beneficial degree, preferably to enhance by at least about 30 percent, more preferably by at least 50 percent, and even more preferable by at least 90 percent. Most preferably the steroid resistance is treated.

The term "steroid" is used to encompass both corticosteroids and glucocorticosteroids. The term "CG containing oligonucleotide" is used to encompass an oligonucleotide having at least one unmethylated CG dinucleotide within its entire sequence length and being preferably 8 to 100 nucleic acid bases in length.

The expression "enhance steroid efficacy" is here used to encompass a steroid sparing effect, evident as a clinical picture where a simultaneous or sequential treatment with a CG containing oligonucleotide, preferably a pre-treatment, is shown to reduce the steroid dose necessary to manage inflammation. The expression "enhance steroid efficacy" is also intended to encompass a synergistic use of a CG containing oligonucleotide and a steroid, either simultaneously or substantially simultaneously, or sequentially or substantially simultaneously, shown to reduce the steroid dose necessary to manage inflammation. The expressions "steroid resistance" or "steroid refractory" are used to encompass a patient failing to respond adequately to a current therapeutic regime deemed to be normally effective and sufficient to treat the disease in question. The expression "steroid dependent" is used to encompass a patient with an observed inability to be weaned off current therapy without compromising the patient status or increasing the severity of the symptoms of the disease in question.

In one aspect, the invention provides pharmaceutical formulations comprising an immunomodulatory oligonucleotide, according to the invention and a physiologically acceptable carrier. As used herein, the term "physiologically acceptable" refers to a material that does not interfere with the effectiveness of the immunomodulatory oligonucleotide and is compatible with a biological system such as a cell, cell culture, tissue, or organism. Preferably, the biological system is a living organism, such as a vertebrate.

As used herein, the term "carrier" encompasses any excipient, diluent, filler, salt, buffer, stabilizer, solubilizer, lipid, or other material well known in the art for use in pharmaceutical formulations. It will be understood that the characteristics of the carrier, excipient, or diluent will depend on the route of administration for a particular application. The preparation of pharmaceutically acceptable formulations containing these materials are described in, e.g., Remington's Pharmaceutical Sciences, 18th Edition, ed. A. Gennaro, Mack Publishing Co., Easton, Pa., 1990.

The concentration of an immunomodulating oligonucleotide in a pharmaceutically acceptable mixture will vary depending on several factors, including the dosage of the compound to be administered, the pharmacokinetic characteristics of the compound(s) employed, the age, sex and condition of the patient, as well as the route of administration. Effective amounts of immunomodulating oligonucleotides for enhancing steroid efficacy in a steroid resistant or steroid dependent patient would broadly range between about 0.01 µg to about 100 mg per kg of body weight, preferably about 0.1 µg to about 10 mg, and most preferably about 1 µg to about 5 mg per kg of body weight of a recipient mammal.

In certain preferred embodiments, immunomodulatory oligonucleotide, according to the invention are administered in combination with, but not limited to, anti-inflammatory agents such as TNF-anti-bodies, non-steroidal anti-inflammatory drugs (NSAIDs) such as ibuprofen, naproxen aspirin and other salicylates and cox-2 inhibitors, such as celecoxib (Celebrex®), corticosteroids (inhaled, oral, rectal), mast cell stabilizers, and leukotriene modifier drugs.

For purposes of this aspect of the invention, the term "in combination with" means in the course of treating the same disease in the same patient, and includes administering the immunomodulatory oligonucleotide in any order, including simultaneous administration, as well as temporally spaced order of up to several months apart. Such combination treatment may also include more than a single administration of the immunomodulatory oligonucleotide. More preferable the immunomodulatory oligonucleotide of the invention is given to a steroid resistant or steroid dependent patient after that patient has started steroid therapy, and is on a stable dosing regime.

In one embodiment the present invention relates to a method for enhancing steroid efficacy in a steroid refractory patient afflicted with an inflammatory condition not responding or responding poorly or inadequately to anti-inflammatory treatment, wherein an oligonucleotide having the sequence $$5'\text{-}X_m\text{-}CG\text{-}Y_n\text{-}3'$$

is administered in an effective amount to said patient and wherein X is A, T, C or G, Y is A, T, C, or G, m=1-100, n=1-100 and wherein at least one CG dinucleotide is ummethylated. In another embodiment of the inventive method m is 1-80 and n is 1-80, m is 1-60 and n is 1-60, m is 1-40 and n is 1-40, m is 1-20 and n is 1-20, m is 1-12 and n is 1-12, m is 1-10 and n is 1-10, m is 1-8 and n is 1-8, m is 1-6 and n is 1-6, m is 1-4 and n is 1-4 or m is 1-2 and n is 1-2.

Oligonucleotides to be used according to the present invention are also exemplified in Table 1.

In the method according to the present invention the patient is currently on corticosteroid treatment, the patient is steroid dependent and currently on corticosteroid treatment or the patient is currently on anti-inflammatory treatment.

In one embodiment of the inventive method the oligonucleotide is administered in combination with steroids.

The method according to the invention is for enhancing steroid efficacy in a patient afflicted with an inflammatory condition. The inflammatory condition is selected from the group consisting of ulcerative colitis (UC), Crohn's disease (CD), rheumatoid arthritis, psoriasis, emphysema, asthma and chronic obstructive pulmonary disease (COPD). In one embodiment the inflammatory condition is ulcerative colitis and in another embodiment the inflammatory condition is Crohn's disease.

The oligonucleotide used in the inventive method can be modified according to methods known for the skilled person and as defined above. For example, at least one nucleotide of the oligonucleotide has a phosphate backbone modification, wherein the phosphate backbone modification is a phosphorothioate or phosphorodithioate modification. The modification can occur at one or more nucleotides at any position along the entire length of the oligonucleotide. In one embodiment the nucleic acid backbone includes the phosphate backbone modification on the 5' inter-nucleotide linkages. As an alternative the nucleic acid backbone includes the phosphate backbone modification on the 3' inter-nucleotide linkages.

In addition to DNA the oligonucleotide can be composed of an analogue or mimic of DNA, including but not restricted to the following: methylphosphonate, N3'->P5'-phosphoramidate, morpholino, peptide nucleic acid (PNA), locked nucleic acid (LNA), arabinosyl nucleic acid (ANA), fluoroarabinosyl nucleic acid (FANA) methoxy-ethyl nucleic acid (MOE).

Further, the oligonucleotide used in the inventive method can comprise at least one modified sugar moiety nucleobase as defined above. The modified sugar moiety is, for example, a 2'-O-methoxyethyl sugar moiety.

The present invention also relates to the use of an oligonucleotide having the sequence:

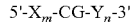

for the manufacture of a medicament for enhancing steroid efficacy in a steroid refractory patient afflicted with an inflammatory condition not responding or responding poorly or inadequately to anti-inflammatory treatment, wherein X is A, T, C or G, Y is A, T, C or G; m=1-100, n=1-100 and wherein at least one CG dinucleotide is unmethlyated. In another embodiment m is 1-80 and n is 1-80, m is 1-60 and n is 1-60, m is 1-40 and n is 1-40, m is 1-20 and n is 1-20, m is 1-12 and n is 1-12, m is 1-10 and n is 1-10, m is 1-8 and n is 1-8, m is 1-6 and n is 1-6, m is 1-4 and n is 1-4 or m is 1-2 and n is 1-2.

The oligonucleotides used in the method as defined above can also be used for the manufacture of the medicament.

In the use according to the present invention the patient is currently on steroid treatment, the patient is steroid dependent and currently on steroid treatment or the patient is currently on anti-inflammatory treatment. In one embodiment the oligonucleotide is administered in combination with steroids.

The inflammatory condition is selected from the group consisting of ulcerative colitis (UC), Crohn's disease (CD), rheumatoid arthritis, psoriasis, emphysema, asthma and chronic obstructive pulmonary disease (COPD). In one embodiment the inflammatory condition is ulcerative colitis and in another embodiment the inflammatory condition is Crohn's disease.

The immunomodulatory oligonucleotide of the invention is illustrated by SEQ.ID.No 1 and serves as an example of immunomodulatory DNA based oligonucleotides containing a CpG motif. The invention disclosed the surprising finding that when such immunomodulatory oligonucleotide as denoted by SEQ.ID.NO.1 is administered to a patient suffering from an inflammatory condition of the bowel (i.e ulcerative colitis and Crohns disease), and who were equally not responding to steroid therapies and were on concomitant steroid therapy, there was a rapid and pronounced improvement of such patients and the dose of administered steroids could be reduced. By contracts when said immunomodulatory oligonucleotide was given to patients suffering from ulcerative colitis where steroids were excluded and the patients were steroid responsive, no improvement in their disease was seen. This surprising observation clearly indicated that through as of yet unknown mechanisms, the immunomodulatory effects of a CpG containing oligonucleotide in the context of steroid resistance induced an improvement of disease that was not apparent in patients that were not steroid resistant.

The following examples firstly confirm that SEQ.ID.NO.1 functions as an immunomodulatory oligonucleotide and that varying lengths of SEQ.ID.NO.1 retain activity. The latter examples are summaries of clinical data in patients with ulcerative colitis and Crohns disease receiving a single rectal administration of SEQ.ID.NO.1.

EXAMPLES

Materials and Methods

Oligodeoxynucleotides (ODN).

In the invention numerous ODNs were used for stimulation experiments using human peripheral blood monocytes (PBMC) or mouse splenocytes. The ODNs used are listed in Table 1. In some of the oligonucleotides the dinucleotide motif was "reversed", and as such function as controls

TABLE 1

Immunomodulatory oligonucleotides

| Compound ID | Sequence ID | Oligo sequence (5'-3') |
|---|---|---|
| DIMS0150 | SEQ. ID. NO. 1 | G*G*A*ACAGTTCGTCCAT*G*G*C |
| IDX0526 | SEQ. ID. NO. 2 | G*G*A*ACAGTTGCTCCAT*G*G*C |
| IDX0304 | SEQ. ID. NO. 3 | A*G*C*TGAGTAGCCTATA*G*A*C |
| IDX0900 | SEQ. ID. NO. 4 | G*G*TGCATCGATGCAG*G*G*G*G*G |
| IDX0910 | SEQ. ID. NO. 5 | T*C*G*T*C*G*T*T*T*TG*T*C*G*T*T*T*T*G*T*C*G*T*T |

TABLE 1-continued

Immunomodulatory oligonucleotides

| Compound ID | Sequence ID | Oligo sequence (5'-3') |
|---|---|---|
| IDX0915 | SEQ. ID. NO. 6 | T*G*C*T*G*C*T*T*T*T*G*T*G*C*T*T*T*T*G*T*G*C*T*T |
| IDX0250 | SEQ. ID. NO. 7 | G*A*A*ACAGATCGTCCAT*G*G*T |
| IDX0254 | SEQ. ID. NO. 8 | G*A*A*ACAGATGCTCCAT*G*G*T |
| IDX0920 | SEQ. ID. NO. 9 | T*C*C*A*T*G*A*C*G*T*T*C*C*T*G*A*C*G*T*T |
| IDX0925 | SEQ. ID. NO. 10 | T*C*C*A*T*G*A*G*C*T*T*C*C*T*G*A*G*C*T*T |

Key
*indicates phosphorothioate linkage while others have phosphodiester linkage.

Formulation

All ODNs, except for DIMS0150 and IDX0250 synthesized by Avecia, were synthesized and delivered by Biomers.net, Germany.

The lyophilized ODNs used (see Table 1)—all except human DIMS0150—were first diluted in a small volume of distilled water. After thorough mixing, each ODN was further diluted with water in a series of different dilutions. The optical density (OD) A260/A280 was determined in at least five or more samples of each dilution using a spectrophotometer (SmartSpec 3000, BioRad). The average concentration of all readings, for all dilutions, was calculated in order to determine the concentration of the stock. These stock solutions were all stored at −20° C. For all ODNs, one portion of the concentrated stock solution was diluted further, in order to obtain one high and one low concentrated stock solution (1 μg/μl and 20 μg/μl respectively). The concentration was determined in the same manner, measuring OD using a spectrophotometer as mentioned above.

The different working solutions used in the experiments; 0.1 μM, 1 μM, 3 μM, 5 μM, 10 μM, 25 μM, 50 μM, 100 μM, 150 μM, 200 μM and 300 μM were prepared by diluting the ODNs further in PBS using the high concentrated stock solution (20 μg/μl) and the low concentrated stock solution (1 μg/μl).

DIMS0150 was diluted in distilled water and the concentration was determined in a similar way as mentioned for the lyophilized ODNs.

Biological Systems
Cell Preparation:

Blood samples were obtained from healthy volunteers. PBMC were isolated by density gradient centrifugation using Ficoll-Paque Plus (Pharmacia Biotech, Uppsala, Sweden), washed three times in buffered saline solution (PBS), and resuspended in RPMI 1640 (Sigma) containing 10% heat inactivated fetal calf serum (FCS) (Life Technologies), 100 U/ml penicillin, 100 μg/ml streptomycin (Life Technologies), 2 mM L-glutamine (Sigma), gentamycin (Sigma) and 5 mM Hepes (Gibco, Life Technologies). Cells were counted using 0.4% Trypan blue solution (Sigma Aldrich)

Mouse Splenocyte Preparation:

For each experiment a spleen was excised from a C57 BL/6 mouse (mice were ordered from MTC animal unit, Karolinska Institutet) and a single cell suspension prepared under sterile conditions by using a nylon cell strainer (Cell strainer 100 μM, BD Falcon). Cells were then washed once in complete RPMI 1640 (RPMI 1640 containing 5% heat inactivated FCS, 2 mM L-glutamine, 100 U/ml penicillin and 100 μg/ml streptomycin) at 1200 rpm for 7-10 minutes. The supernatant was decanted and cells were resuspended in 1 ml red blood cell lysing buffer (Sigma) and incubated for a maximum of two minutes at room temperature. Another 5 ml complete medium was added before centrifugation performed as previously described. After decanting the supernatant, cell pellet was resuspended in complete medium and cell numbers were determined in 0.4% Trypan blue solution.

Techniques
ELISpot

PBMC, as described previously, were seeded into a pre-coated, PVDF-based membrane plate for ELISpot (MABTech AB, Sweden). Prior to cell addition the PDVF-plate was coated overnight at +4° C. with a specific coating-antibody for IFN-alpha, IFN-gamma or IL-10 (included in ELISpot kits; IFN-alpha, IFN-gamma and IL-10 from MABTech AB, Sweden) respectively. PBMC were then seeded at 500 000 cells/well in complete RPMIc. Directly after seeding, cells were treated with the respective oligonucleotides (ODN). Each ODN was added to the specific wells giving final ODN-concentrations of 0.1, 1, 5, 10, 25, 50, 100, 150 and 200 μM in a total volume of 100 μl/well. Samples were prepared in triplicates. After treatment, cells were incubated in a humified incubator at 5% carbon dioxide at 37° C. IFN-alpha was analyzed for 2, 10 and 3 donors at 24, 48 and 72 hrs, respectively. IFN-gamma was analyzed for 2, 7 and 5 donors at 24, 48 and 72 hrs, respectively. IL-10 was analyzed for 5 and 4 donors at 48 and 72 hrs, respectively. Detection and counting of cytokine producing cells was performed by following the manufacturer's manual. The ELISpot reader software was AID 2.3.3 located at Center for Molecular Medicine, CMM, Karolinska Hospital, Solna, Sweden.

Enzyme-Linked ImmunoSorbent Assay—ELISA

PBMC, prepared as described previously, were seeded into a 96-well flat bottomed cell culture plate at 500 000 cells/well in RPMIc. Directly after seeding, cells were treated with the respective ODN. Each ODN was added to the specific wells giving final ODN-concentrations between 0.1, 1, 5, 10, 25, 50, 100, 150, 200 and 300 μM in a total volume of 100 μl/well. Samples were prepared in duplicates. After treatment, cells were incubated in a humified incubator at 5% carbon dioxide and 37° C. for 48 hrs. Supernatants were saved and stored at −20° C. prior to cytokine level determination by using specific Quantikine ELISA following the manufacturer's protocol (For human PBMC experiments the following ELISA kits were used: human IL-10 and human IFN-alpha. For mouse splenocytes experiments; murine IL-10; murine IFN-alpha, R&D Systems, Abingdon, UK).

Example 1

Evaluation of Cytokine Production of PBMC Upon Stimulation with DIMS0150

Figure 2:
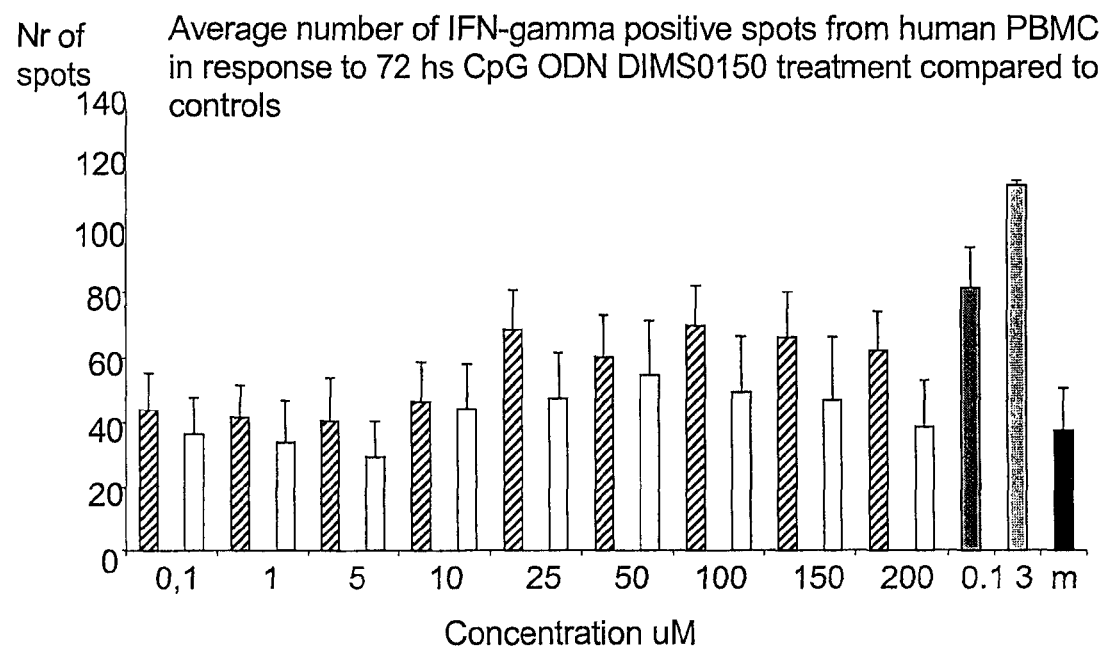
FIG. 2 is a graph showing the number of IFN-gamma producing cells in response to 72 hrs of DIMS0150 stimulation of PBMC from five (n=5) different donors as analysed by ELISpot. PBMC were incubated in medium (basal) or with increasing concentrations (0.1, 1, 5, 10, 25, 50 100, 150 or 200 μM) of the CpG containing DIMS0150, or its GpC control IDX0526, or the CpG ODNs IDX0910 (at 0.1 μM) and IDX0900 (at 3 μM) for 72 hours before detection of IFN-gamma positive spots. Each bar of the histogram represents the average results from five different blood donors. Samples were performed and analysed in triplicate for each experiment/blood donor. Note that IDX0900 was tested on three individuals (n=3).
Figure 3:
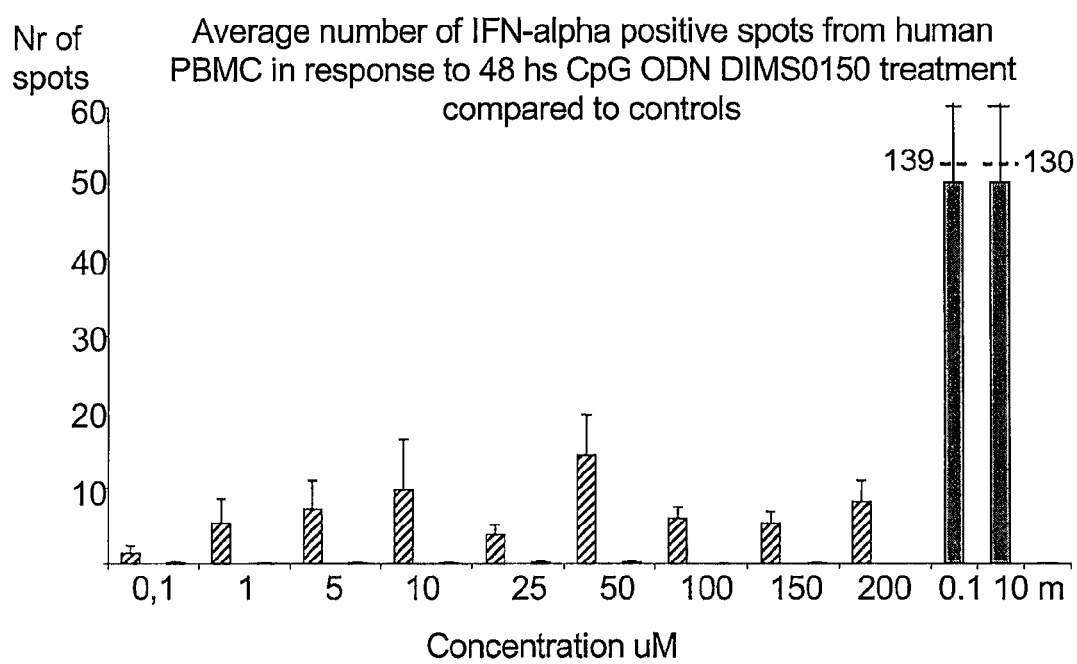
FIG. 3 is a graph showing the number of IFN-alpha producing cells in response to 48 hrs DIMS0150 in PBMC from ten (n=10) different healthy donors as assayed by ELISpot. PBMC were incubated in medium (basal) or with increasing concentrations (0.1, 1, 5, 10, 25, 50, 100, 150 or 200 μM) of the CpG containing DIMS0150, or its GpC control IDX0526 (n=9) or the CpG ODN IDX0910 (0.1 μM or 10 μM) for 48 hours before detection of IFN-alpha positive spots. Each bar of the histogram represents the average results from ten different blood donors. Samples were performed and analysed in triplicate for each experiment/blood donor. Note that IDX0910 at 0.1 μM was tested on eight donors and 10 μM was tested on four individuals.

The immunostimulatory activity of the CpG containing ODN, DIMS0150, was evaluated in human PBMC. The hypothesis was that PBMC incubated with different concentrations of DIMS0150 for different periods of time would stimulate cytokine production in a CpG dependent manner. For this reason, three cytokines that are well known to be produced by PBMC in response to CpG DNA, namely IFN-alpha, IL-10 and IFN-gamma were chosen. Indeed, PBMC from different healthy donors all showed time (data not shown) and dose dependent cytokine production as analysed by ELISpot in response to DIMS0150. Among the three cytokines tested, IL-10 was the most responding cytokine after 48 hrs stimulation with DIMS0150 (FIG. 1.). In contrast to IL-10, DIMS0150 was less potent at inducing IFN-alpha and IFN-gamma in PBMC at all concentrations and time points tested, represented by 72 hrs for IFN-gamma (see FIG. 2) and 48 hrs for IFN-alpha (see FIG. 3). A CpG reverted form of DIMS0150, IDX0526, was also included in all experiments in order to evaluate the CpG dependency of potential cytokine production. PBMC treated with the IDX0526 showed no or reduced production of all three cytokines studied compared to stimulation with DIMS0150 (see FIGS. 1, 2 and 3).

Example 2

Quantification of Cytokine Production of PBMC in Response to DIMS0150

Figure 4A:
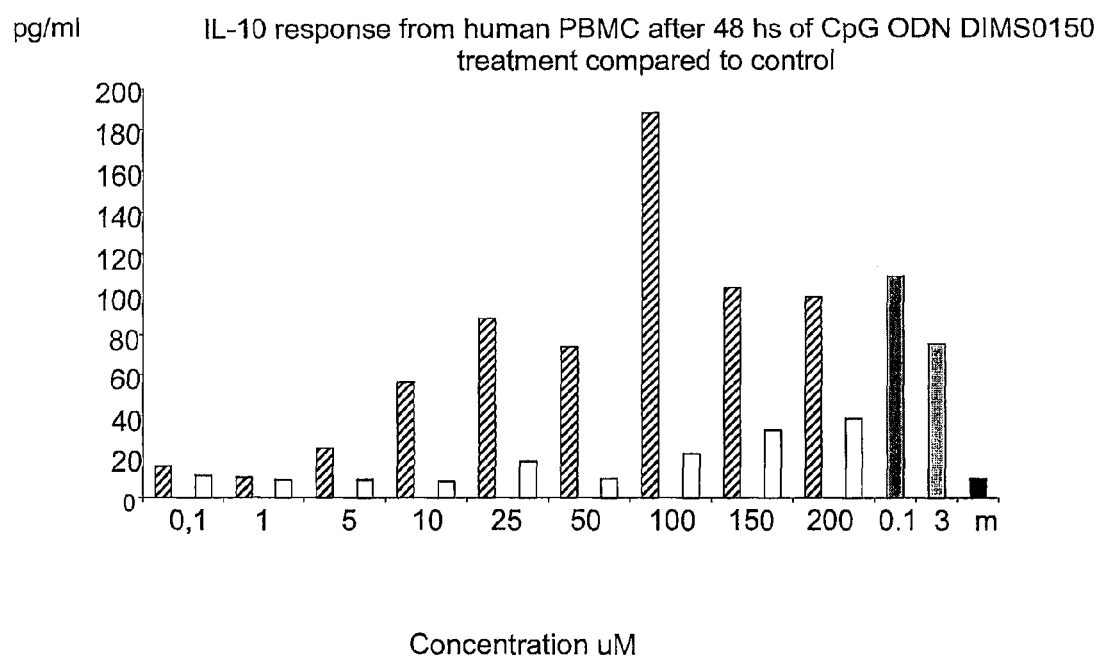
FIG. 4A is a graph showing the IL-10 production in response to 48 hrs stimulation with DIMS0150 as quantified by ELISA. PBMC were incubated with increasing concentrations (0.1, 1, 5, 10, 25, 50, 100, 150 or 200 μM) of DIMS0150 or its GpC control IDX0526. As controls, cells were left in medium (basal) or treated with CpG ODNs IDX0910 (0.1 μM) and IDX0900 (3 μM). This graph represents results from an experiment in PBMC from one of two donors performed and analysed in duplicate.
Figure 4B:
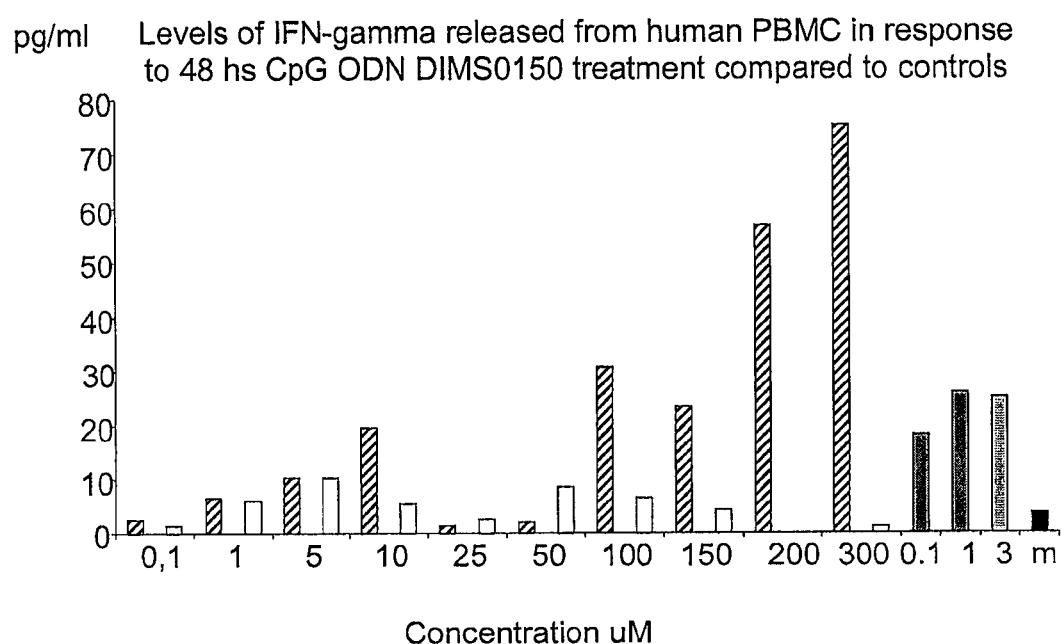
FIG. 4B is a graph showing the IFN-gamma production in response to 48 hrs stimulation with DIMS0150 as quantified by ELISA. PBMC were incubated with increasing concentrations (0.1, 1, 5, 10, 25, 50, 100, 150, 200 or 300 μM) of DIMS0150 or its GpC control IDX0526. As controls, cells were left in medium (basal) or treated with CpG ODNs, IDX0910 (0.1 μM and 1 μM) or IDX0900 (3 μM). This experiment was performed in cells from one blood donor and each sample was performed and analysed in duplicate.
Figure 4C:
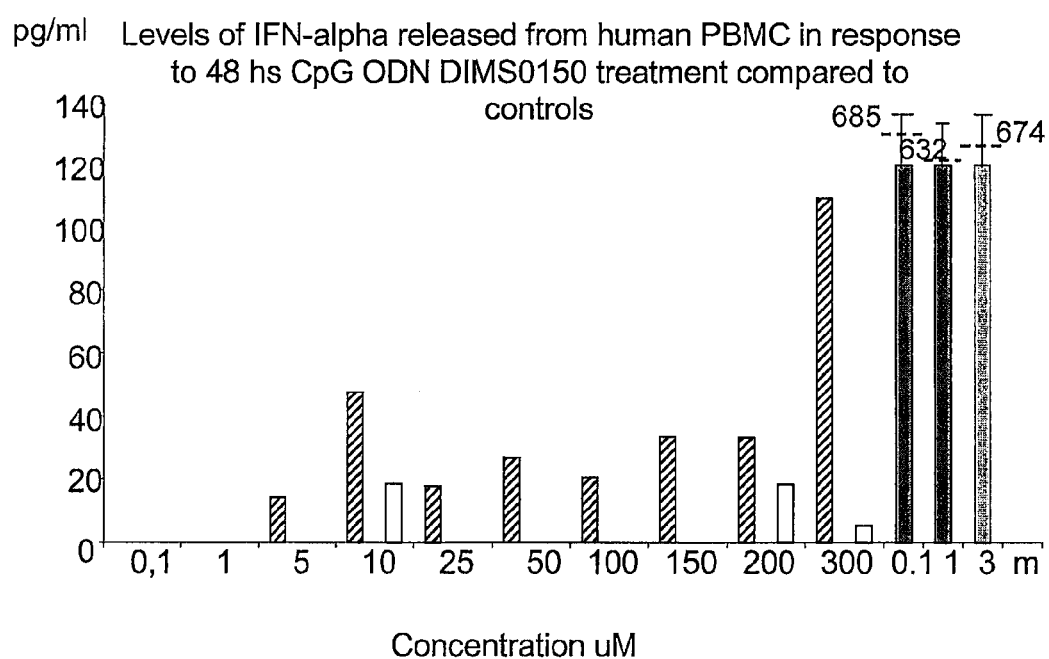
FIG. 4C is a graph showing the IFN-alpha production in response to 48 hrs stimulation with DIMS0150 as quantified by ELISA. PBMC were incubated with different concentrations (0.1, 1, 5, 10, 25, 50, 100, 150, 200 or 300 μM) of DIMS0150 or its GpC control IDX0526. As controls, cells were left in medium (basal) or treated with CpG ODNs, IDX0910 (0.1 μM and 1 μM) and IDX0900 (3 μM). This graph represents results from an experiment in PBMC from one of two donors performed and analyzed in duplicate.

In order to quantify the amount of cytokine produced from the positive cells observed by ELISpot, ELISA analyses were performed. PBMC were incubated with increasing concentrations of DIMS0150 and the supernatants were analyzed for levels of IL-10, IFN-alpha and IFN-gamma. In agreement with those results obtained by ELISpot data, using concentrations between 0.1 and 200 µM (or 300 µM for IFN-alpha and IFN-gamma) resulted in a CpG dependent dose response of all the cytokines after 48 hrs incubation (see FIGS. 4 A, B and C). Since ELISpot and ELISA measure different parameters (i.e. number of cells secreting a particular cytokine versus the amount of secreted cytokine) the ELISA measurements should be considered as complementary information regarding the actual amount being produced at an particular concentration, regardless of the number of cells secreting the cytokine of interest. Thus, the dose response pattern may appear different when comparing results from those different techniques. The individual variance in response to DIMS0150 as analysed by quantitative ELISA has been less extensively investigated (1-3 donors), in comparison to ELISpot.

Example 3

Comparison of DIMS0150 with Different CpG ODNs in PBMC

Figure 5:
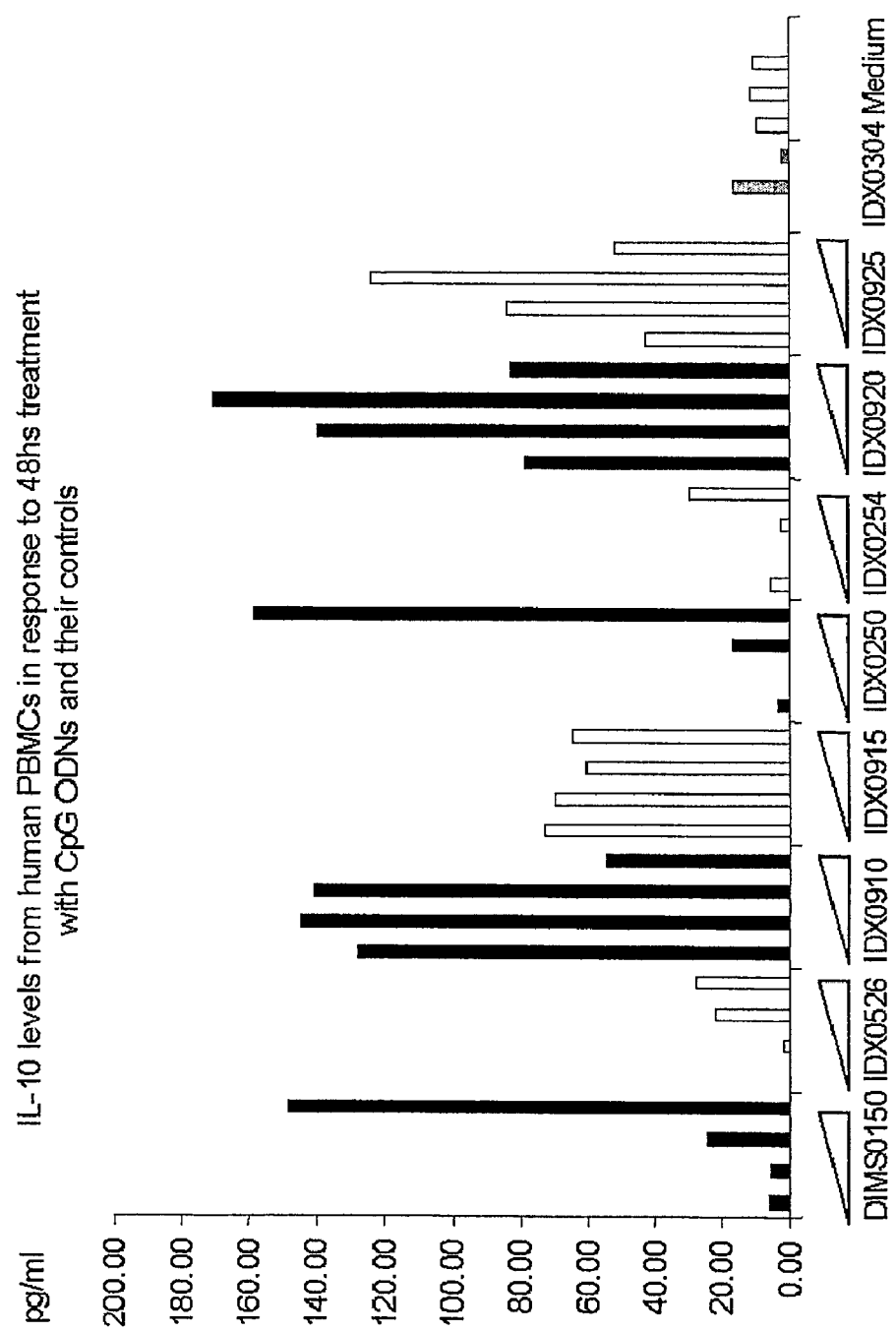
FIG. 5 is a graph showing the comparison of IL-10 production in human PBMC upon stimulation with a variety of CpG ODNs and their reversed controls as quantified by ELISA. PBMC were treated with increasing concentrations (from left to right, as indicated by the triangle: 0.1, 1, 10 or 100 μM) of DIMS0150, IDX0250, IDX0920 and IDX 0910 ODNs and their respective negative control GpC ODNs together with the non-CpG containing ODN IDX0304 for 48 hours before collection of supernatants and subsequent analysis. Cells left untreated in medium exhibited the basal level of IL-10 in PBMC. Supernatants were collected after 48 hours followed by subsequent analysis. This experiment was performed on cells from one blood donor and all samples were performed and analysed in duplicate.
Figure 6:
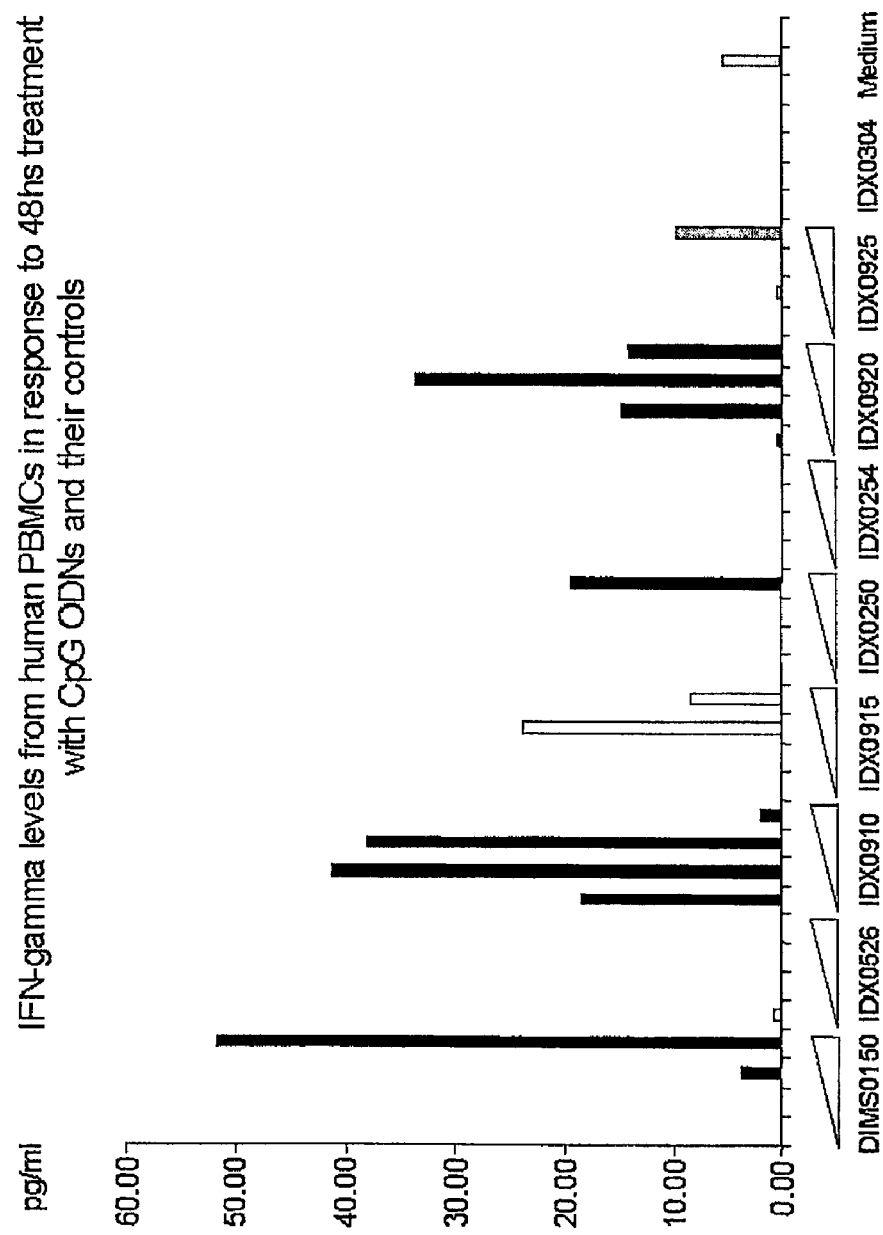
FIG. 6 is a graph showing the comparison of IFN-gamma production in human PBMC upon stimulation with a variety of CpG ODNs as quantified by ELISA. PBMC were treated with increasing concentrations (from left to right, as indicated by the triangle: 0.1, 1, 10 or 100 μM) of DIMS0150, IDX0250, IDX0920 and IDX 0910 ODNs and their respective negative control GpC ODNs together with the non-CpG containing ODN IDX0304 for 48 hours before collection of supernatants and subsequent analysis. Cells left untreated in medium exhibited the basal level of IFN-gamma in PBMC. Supernatants were collected after 48 hours followed by subsequent analysis. This experiment was performed on cells from one blood donor and all samples were performed and analysed in duplicate.

A dose response of DIMS0150 stimulation was compared with that of known human and murine CpG ODNs, IDX0910 and IDX0920, respectively. In addition, IDX0250 was also included in this experimental set up, since this ODN sequence also contains a CpG dinucleotide and may act as CpG DNA. The CpG flanking bases in IDX0250 differ slightly to DIMS0150 and this may influence the level of cytokine response in PBMC upon stimulation. In this investigation, PBMC were treated for 48 hours with the CpG ODNs and their respective reversed GpC controls before supernatants were analyzed in duplicate using quantitative ELISA assays for IL-10 and IFN-gamma DIMS0150 and the IDX0250 gave rise to a similar IL-10 response at 100 µM (FIG. 5.) but at the lowest concentrations (0.1 µM to 1 µM), none of these ODNs stimulated IL-10 production of PBMC. In comparison, PBMC incubation with IDX0910 or IDX0920 reached the highest IL-10 production at the lower concentrations used. IFN-gamma analysis of the supernatants resulted in lower secretion of this cytokine compared to IL-10 (FIG. 6). None of the GpC reversed controls or IDX0304 induced IFN-gamma but some levels of IL-10 secretion in PBMC were observed with the two control GpC ODNs, IDX0915 and IDX0925. This may be due to the presence of a fully phosphorothioate backbone in those ODNs.

Example 4

Comparison of DIMS0150 with Different CpG ODNs in Mouse Splenocytes

Figure 7:
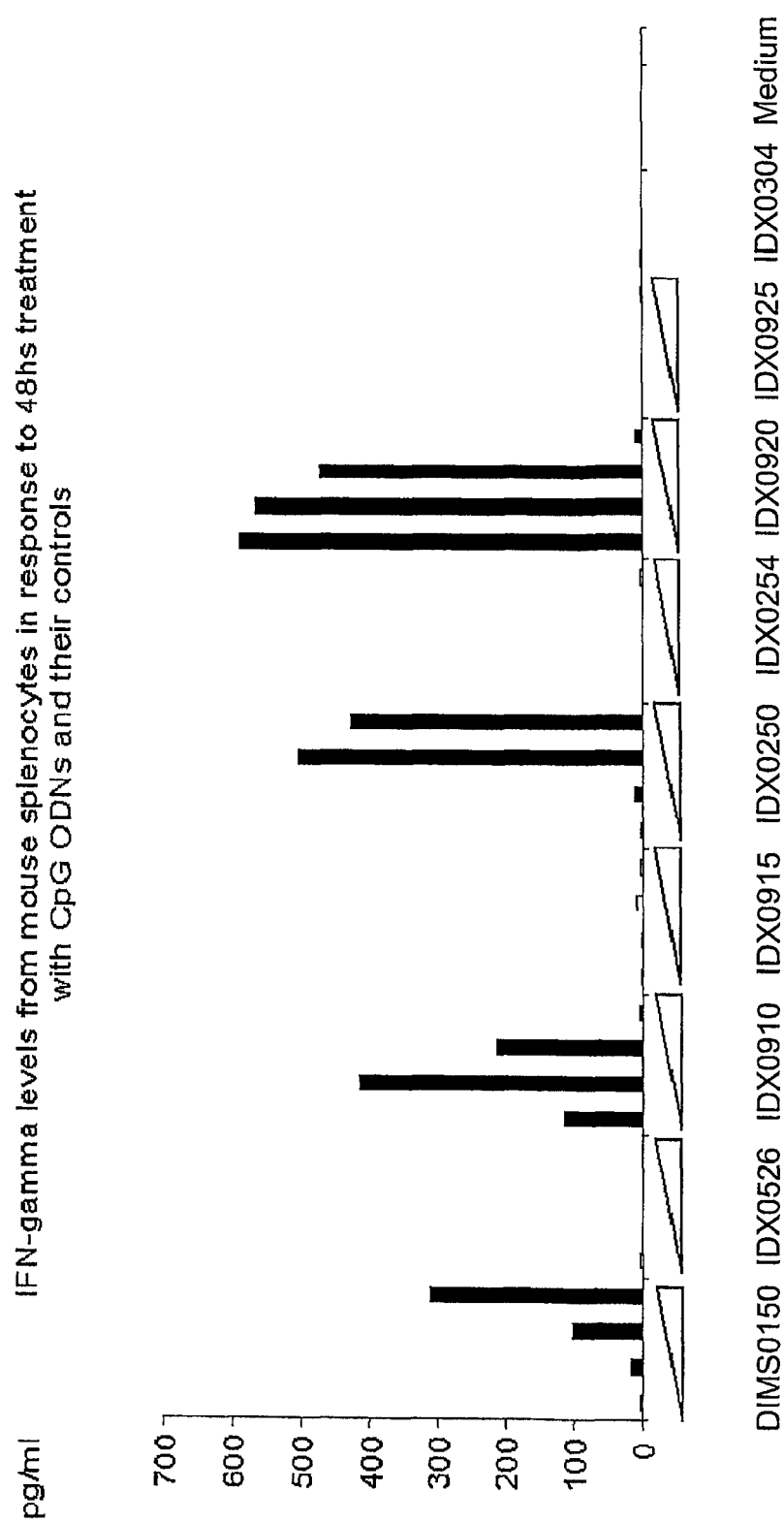
FIG. 7 is a graph showing the IFN-gamma production from mouse splenocytes in response to 48 hs of CpG-stimulation as quantified by ELISA. Mouse splenocytes were treated with increasing concentrations (from left to right, as indicated by the triangles: 0.1, 1, 10 or 100 μM) of DIMS0150, IDX0250, IDX0920, IDX0910 ODNs and their respective negative control GpC ODNs compared to the non CpG-containing ODN control IDX0304 for 48 hours before collection of supernatants and subsequent analysis. Cells left untreated in medium exhibit the basal level of IFN-gamma in splenocytes. Supernatants were collected after 48 hours of stimulation followed by subsequent analysis. Note that this experiment was performed in cells from one mouse spleen and all samples were performed and analyzed in duplicate.
Figure 8:
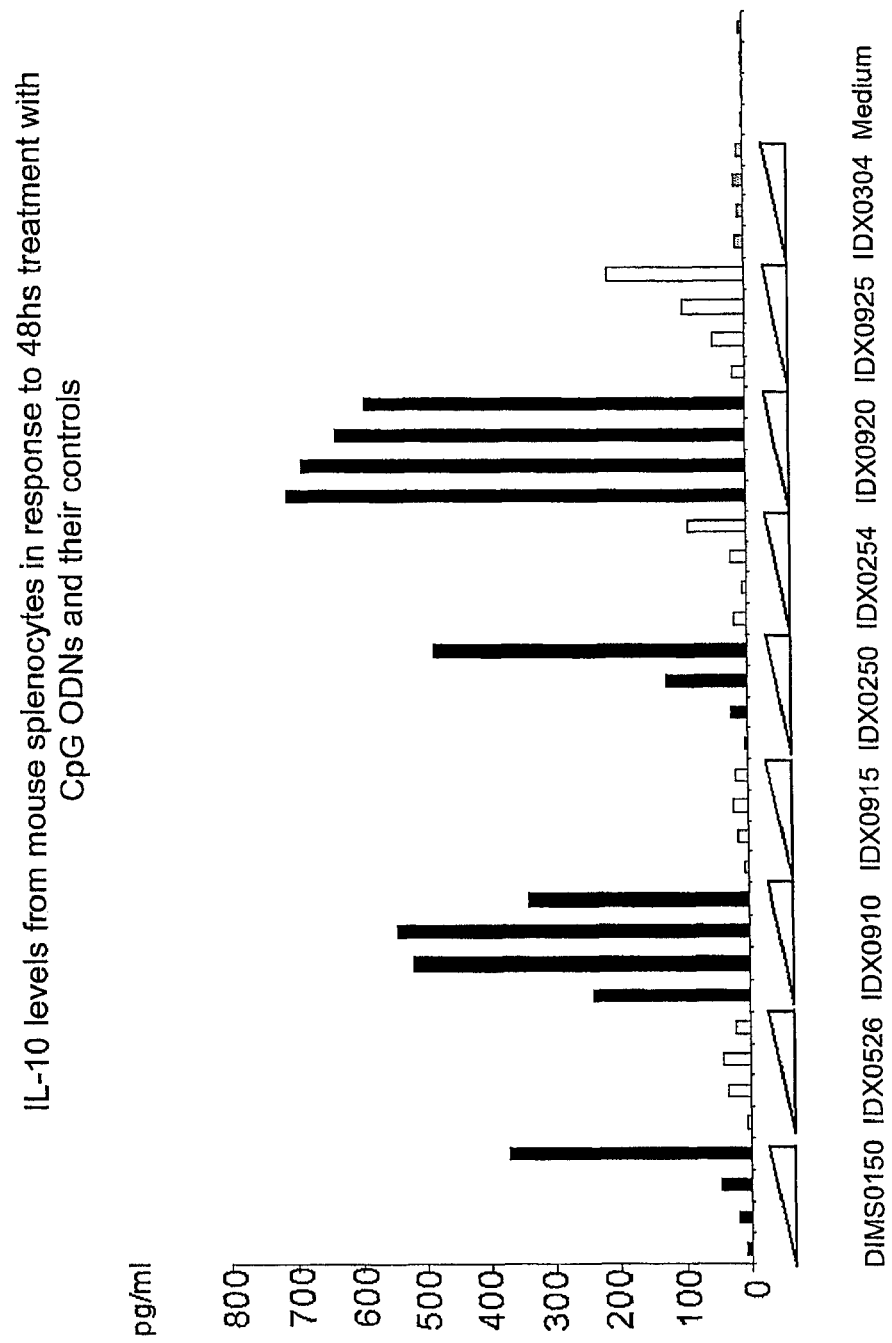
FIG. 8 is a graph showing the IL-10 production from mouse splenocytes in response to 48 hs of CpG-stimulation as quantified by ELISA. Mouse splenocytes were treated with increasing concentrations (from left to right, as indicated by the triangle: 0.1, 1, 10 or 100 μM) of DIMS0150, IDX0250, IDX0920 and IDX 0910 ODNs and their respective negative control GpC ODNs together with the non-CpG containing ODN IDX0304 for 48 hours before collection of supernatants and subsequent analysis. Cells left untreated in medium exhibited the basal level of IL-10 in splenocytes. Supernatants were collected after 48 hours followed by subsequent analysis. This experiment was performed on cells from one mouse spleen and all samples were performed and analysed in duplicate.

Humans and mice respond to different CpG ODNs. The immunostimulatory effect of DIMS0150 was compared to the same set of CpG ODNs performed in PBMC (see FIG. 6) in a mouse splenocyte system. Splenocytes were treated with CpG ODNs and their respective reversed negative GpC control for 48 hours before supernatants were analyzed for IFN-gamma and IL-10 in duplicate using quantitative ELISA assays. Treatment of splenocytes with DIMS0150 resulted in a strong IFN-gamma response at the highest concentration used. However, in this assay IDX0250 was more potent than DIMS0150, indicating that sequences surrounding the CpG also have impact on level of response (FIG. 7). The most pronounced IFN-gamma levels was found in supernatants from cells stimulated with the CpG ODN, IDX0920 at the lower concentrations used. Lastly, analysing the supernatants for levels of IL-10 (FIG. 8.) showed similar pattern to what was observed when measuring IFN-gamma. None of the GpC reversed ODN controls induced IFN-gamma, but IDX0925 induced some level of IL-10 also in the murine system.

Example 5

Human Pilot Proof of Concept Study

The Pilot proof of concept study is described in its entirety in Annex I.
Aims of the Study:
Primary objective: To assess the safety issues regarding the use of the DNA based oligonucleotide denoted as SEQ.ID.No 1 in ulcerative colitis and Crohns disease patients.
Secondary objective: To explore the clinical efficacy as determined by endoscopic and clinical remission/improvement rates, histological improvement and changes in clinical laboratory parameters.
The study was placebo controlled; double blinded single dose and considered patients that were unresponsive to corticosteroids or corticosteroid dependent who where on concomitant steroid therapies.
Doses levels used were 3 mg and 30 mg given as a single rectal administration
Clinical Response at Week 1

| i)  | SEQ. ID. NO. 1 | 5/7 (71%) responders |
| ii) | Placebo        | 1/4 (25%) responders |

Overall, this pilot study indicated good efficacy in both dose groups following a single rectal administration. Perhaps more suspiring was the rapidity of response in that all responding patients did so within a week of receiving the study drug. Of interest was the finding that two from the 7 patients that received SEQ.ID.NO.1 are still as of today in remission and steroid free. Moreover, no serious adverse events were recorded.

Example 6

Clinical Phase II Study

Aims of the Study

Primary objective: To evaluate the ability of each of the four dose levels (0.3 mg, 3 mg, 30 mg and 100 mg) of oligonucleotide SEQ.ID.NO.1 as an anti-inflammatory therapy to induce clinical remission in patients with mild to moderately active ulcerative colitis (UC), as compared with placebo.

Secondary objective: To assess the tolerability of single rectal doses of SEQ.ID.NO.1 oligonucleotide and to further evaluate the efficacy and safety of SEQ.ID.NO.1 oligonucleotide at four dose levels and to assess the pharmacokinetics of SEQ.ID.NO.1 oligonucleotide after rectal administration, as compared to placebo.

Study Conclusions:
Clinical Response at Week 1, ITT/Safety Population

| Clinical Response | 0.3 mg (N = 31) | 3 mg (N = 29) | 30 mg (N = 30) | 100 mg (N = 29) | Placebo (N = 29) |
|---|---|---|---|---|---|
| Yes, n (%) | 8 (25.8) | 6 (20.7) | 7 (23.3) | 5 (17.2) | 11 (37.9) |
| No, n (%) | 23 (74.2) | 23 (79.3) | 23 (76.7) | 24 (82.8) | 18 (62.1) |

From the table response rate to those receiving active drug was 22% ($26/119$), placebo was 38% ($11/29$). This study could not confirm that one single dose of SEQ.ID.NO.1 oligonucleotide in doses from 0.3 to 100 mg in a limited number of patients, can induce clinical, endoscopic or histopathological remissions or responses over a 12 week period, however, this study demonstrated a good safety profile of the drug.

In Comparison Clinical Response Rates at Week 1

|  | Pilot study | Phase II |
|---|---|---|
| Active | 71% | 22% |
| Placebo | 25% | 38% |

It is apparent that patients from the pilot study had a much better response rate than that seen in phase II. It is also clear that while patients from the pilot study where allowed steroids as concomitant medications and where resistant or dependent on corticosteroids, it was an exclusion criteria in phase II. No steroids were allowed during the duration of the phase II study and the patients were neither resistant nor dependent on steroid therapies.

The diverging results between the pilot study and larger phase II study would suggest that patients that are resistant or dependent on corticosteroids and on concomitant corticosteroid therapy respond more favourably to a single rectal dose of SEQ.ID.No 1 than those patients that are not. The reason for this surprising difference in clinical outcome is not clear. However, the immunomodulating action of CpG containing oligonucleotides could induce beneficial changes to the patient's immune system such that steroid resistant or steroid dependent patients were able to respond to steroids again. In other words, immunomodulating oligonucleotides may induce a re-sensitization of the patients to the anti-inflammatory effects of steroids.

The provided examples confirm that immunomodulatory oligonucleotides that contain a CpG dinucleotide within their sequence such as example SEQ.ID.NO.1 are able to induce certain cytokines for which there exists evidence of their role in modulating steroid responsiveness, as mentioned in background art. In light of such, immunomodulatory oligonucleotides that induce the production of interferons and IL-10, for example, may prove beneficial.

Although particular embodiments have been disclosed herein in detail, this has been done by way of example for purposes of illustration only, and is not intended to be limiting with respect to the scope of the appended claims that follow. In particular, it is contemplated by the inventor that various substitutions, alterations, and modifications may be made to the invention without departing from the spirit and scope of the invention as defined by the claims.

References

Bauer M, Redecke V, Ellwart J W, Scherer B, Kremer J P, Wagner H, Lipford G B. Bacterial CpG-DNA triggers activation and maturation of human CD11c-, CD123+ dendritic cells. J Immunol. 2001 Apr. 15; 166(8):5000-7.

Bennet J D and Brinkman M (1989) Treatment of ulcerative colitis by implantation of normal colonic flora. Lancet 1:164.

Borody T J, Warren E F, Leis S, Surace R, Ashman O. Treatment of ulcerative colitis using fecal bacteriotherapy. J Clin Gastroenterol. 2003 July; 37(1):42-7.

Chikanza I C and Kozaci D L. Corticosteroid resistance in rheumatoid arthritis: molecular and cellular perspectives. Rheumatology 2004 43:1337-1345.

Cowdery J S, Chace J H, Yi A K, Krieg A M. Bacterial DNA induces NK cells to produce IFN-gamma in vivo and increases the toxicity of lipopolysaccharides. J Immunol 1996 Jun. 15; 156(12):4570-5.

Eiseman B, Silen W, Bascom G S et al (1958) Fecal enema as an adjunct in the treatment of pseudomembranous enterocolitis. Surgery. 44:854-859.

Eui-Young So, Hyun-Hee Park and Choong-Eun Lee. IFN-gamma and IFN-alpha post transcriptionally down regulate the IL-4 induced IL-4 receptor gene expression. J of Immunology, 2000 165:5472-5479.

Gill P S, Harrington W Jr, Kaplan M H, Ribeiro R C, Bennett J M, Liebman H A, Bernstein-Singer M, Espina B M, Cabral L, Allen S, et al (1995) Treatment of adult T-cell leukemia-lymphoma with a combination of interferon alfa and zidovudine. N Engl J Med. 332:1744-8.

Hacker H, Mischak H, Miethke T, Liptay S, Schmid R, Sparwasser T, Heeg K, Lipford G B, Wagner H. CpG-DNA-specific activation of antigen-presenting cells requires stress kinase activity and is preceded by non-specific endocytosis and endosomal maturation. EMBO J. 1998 Nov. 2; 17(21):6230-40.

Hamid Q A, Wenzel S E, Hauk P J, Tsicopoulos A, Wallaert B, Lafitte J J, Chrousos G P, Szefler S J, Leung D Y Increased glucocorticoid receptor beta in airway cells of glucocorticoid-insensitive asthma. Am J Respir Crit Care Med. 1999 May; 159(5 Pt 1):1600-4.

Hartmann G, Krieg A M. Mechanism and function of a newly identified CpG DNA motif in human primary B cells. J Immunol 2000 Jan. 15; 164(2):944-53.

Hartmann G, Weiner G J, Krieg A M. CpG DNA: a potent signal for growth, activation, and maturation of human dendritic cells. Proc Natl Acad Sci USA. 1999 Aug. 3; 96(16):9305-10.

Hawrylowicz C M, O'Garra A (2005) Potential role of interleukin-10-secreting regulatory T cells in allergy and asthma. Nat Rev Immunol. 5:271-83.

Hawrylowicz C M, Richards D, Loke T K, Corrigan C, Lee T (2002) A defect in corticosteroid-induced IL-10 production in T lymphocytes from corticosteroid-resistant asthmatic patients. J Allergy Clin Immunol. 109:369-70.

Iho S, Yamamoto T, Takahashi T, Yamamoto S. Oligodeoxynucleotides containing palindrome sequences with internal 5'-CpG-3' act directly on human NK and activated T cells to induce IFN-gamma production in vitro. J Immunol 1999 Oct. 1; 163(7):3642-52.

Jahn-Schmid B, Wiedermann U, Bohle B, Repa A, Kraft D, Ebner C. Oligodeoxynucleotides containing CpG motifs modulate the allergic TH2 response of BALB/c mice to Bet v 1, the major birch pollen allergen. J Allergy Clin Immunol. 1999 November; 104(5):1015-23.

Jakob T, Walker P S, Krieg A M, Udey M C, Vogel J C Activation of cutaneous dendritic cells by CpG-containing oligodeoxynucleotides: a role for dendritic cells in the augmentation of Th1 responses by immunostimulatory DNA. J Immunol 1998 Sep. 15; 161(6):3042-9.

Kline J N. Effects of CpG DNA on Th1/Th2 balance in asthma. Curr Top Microbiol Immunol. 2000; 247:211-25

Klinman D M, Barnhart K M, Conover J. CpG motifs as immune adjuvants. Vaccine. 1999 January; 17(1):19-25.

Krieg. Applied Oligonucleotide Technology. C. A. Stein and A. M. Krieg (Eds.), John Wiley and Sons, Inc., New York, N.Y., 1998, pp. 431-448.

Krieg A M, Yi A K, Matson S, Waldschmidt T J, Bishop G A, Teasdale R, Koretzky G A, Klinman D M. CpG motifs in bacterial DNA trigger direct B-cell activation. Nature 1995 Apr. 6; 374(6522):546-9.

Krieg A M, Matson S, Fisher E. Oligodeoxynucleotide modifications determine the magnitude of B cell stimulation by CpG motifs. Antisense Nucleic Acid Drug Dev 1996 Summer; 6(2):133-9.

Krug A, Towarowski A, Britsch S, Rothenfusser S, Homung V, Bals R, Giese T, Engelmann H, Endres S, Krieg A M, Hartmann G. Toll-like receptor expression reveals CpG DNA as a unique microbial stimulus for plasmacytoid dendritic cells which synergizes with CD40 ligand to induce high amounts of IL-12. Eur J Immunol. 2001 October; 31(10):3026-37.

Mannon P J, Fuss I J, Mayer L, Elson C O, Sandbom W J, Present D, Dolin B, Goodman N, Groden C, Hornung R L, Quezado M, Neurath M F, Salfeld J, Veldman G M, Schwertschlag U, Strober W; Anti-IL-12 Crohn's Disease Study Group. Anti-interleukin-12 antibody for active Crohn's disease. N Engl J Med. 2004 Nov. 11; 351(20):2069-79.

Musch E, Andus T, Malek M. Induction and maintenance of clinical remission by interferon-beta in patients with steroid-refractory active ulcerative colitis—an open long-term pilot trial. Aliment Pharmacol Ther. 2002 July; 16(7):1233-9.

Naseer T, Minshall E M, Leung D Y, Laberge S, Ernst P, Martin R J, Hamid Q. Expression of IL-12 and IL-13 mRNA in asthma and their modulation in response to steroid therapy. Am J Respir Crit Care Med. 1997 March; 155(3):845-51.

Neurath M F, Fuss I, Kelsall B L, Stuber E, Strober W. Antibodies to interleukin 12 abrogate established experimental colitis in mice. J Exp Med. 1995 Nov. 1; 182(5):1281-90.

Niederau C, Heintges T, Lange S, Goldmann G, Niederau C M, Mohr L, Haussinger D. Long-term follow-up of HBeAg-positive patients treated with interferon alfa for chronic hepatitis B. N Engl J Med. 1996 May 30; 334(22):1422-7.

Pisetsky D S. The immunologic properties of DNA. J Immunol. 1996 Jan. 15; 156(2):421-3.

Richards D F, Fernandez M, Caulfield J, Hawrylowicz C M (2005) Glucocorticoids drive human CD8(+) T cell differentiation towards a phenotype with high IL-10 and reduced IL-4, IL-5 and IL-13 production. Eur J Immunol. 30:2344-54.

Simon H U, Seelbach H, Ehmann R, Schmitz M (2003) Clinical and immunological effects of low-dose IFN-alpha treatment in patients with corticosteroid-resistant asthma. Allergy. 58:1250-5.

Smeltz R B, Chen J, Ehrhardt R, Shevach E M. Role of IFN-gamma in Th1 differentiation: IFN-gamma regulates IL-18R alpha expression by preventing the negative effects of IL-4 and by inducing/maintaining IL-12 receptor beta 2 expression. J Immunol. 2002 Jun. 15; 168(12):6165-72.

Sousa A R, Lane S J, Cidlowski J A, Staynov D Z, Lee T H Glucocorticoid resistance in asthma is associated with elevated in vivo expression of the glucocorticoid receptor beta-isoform. J Allergy Clin Immunol. 2000 May; 105(5): 943-50.

Sparwasser T, Koch E S, Vabulas R M, Heeg K, Lipford G B, Ellwart J W, Wagner H. Bacterial DNA and immunostimulatory CpG oligonucleotides trigger maturation and activation of murine dendritic cells. Eur J Immunol 1998 June; 28(6):2045-54.

Stacey K J, Sweet M J, Hume D A. Macrophages ingest and are activated by bacterial DNA. J Immunol 1996 Sep. 1; 157(5):2116-22.

Stelmach I, Jerzynska J, Kuna P (2002) A randomized, double-blind trial of the effect of glucocorticoid, antileukotriene and beta-agonist treatment on IL-10 serum levels in children with asthma. Clin Exp Allergy. 32:264-9.

Sumer N, Palabiyikoglu M (1995) Induction of remission by interferon-alpha in patients with chronic active ulcerative colitis. Eur J Gastroenterol Hepatol. 7:597-602.

Taniguchi T and Takaoka A (2001) A weak signal for strong responses: interferons-alpha/beta revisited. Nat Rev Mol Cell Biol 2:378-386.

Tighe H, Takabayashi K, Schwartz D, Marsden R, Beck L, Corbeil J, Richman D D, Eiden J J Jr, Spiegelberg H L, Raz E. Conjugation of protein to immunostimulatory DNA results in a rapid, long-lasting and potent induction of cell-mediated and humoral immunity. Eur J Immunol. 2000 July; 30(7):1939-47.

Tokunaga T, Yano O, Kuramoto E, Kimura Y, Yamamoto T, Kataoka T, Yamamoto S. Synthetic oligonucleotides with particular base sequences from the cDNA encoding proteins of Mycobacterium bovis BCG induce interferons and activate natural killer cells. Microbiol Immunol. 1992; 36(1):55-66.

Tomitai K, Lim S, Hanazawa T, Usmani O, Stirling R, Chung K F, Barnes P J, Adcock I M (2002) Attenuated production of intracellular IL-10 and IL-12 in monocytes from patients with severe asthma. Clin Immunol. 102:258-66.

Tormey V J, Leonard C, Faul J, Bernard S, Burke C M, Poulter L W (1998) Deregulations of monocyte differentiation in asthmatic subjects is reversed by IL-10. Clin Exp Allergy. 28:992-8.

Xystrakis E, Kusumakar S, Boswell S, Peek E, Urry Z, Richards D F, Adikibi T, Pridgeon C, Dallman M, Loke T K, Robinson D S, Barrat F J, O'Garra A, Lavender P, Lee T H, Corrigan C, Hawrylowicz C M. Reversing the defective induction of IL-10-secreting regulatory T cells in glucocorticoid-resistant asthma patients. J Clin Invest. 2006 January; 116(1):146-55. Epub 2005 Dec. 8.

Yamamoto S, Yamamoto T, Kataoka T, Kuramoto E, Yano O, Tokunaga T. Unique palindromic sequences in synthetic oligonucleotides are required to induce IFN [correction of INF] and augment IFN-mediated [correction of INF] natural killer activity. J Immunol. 1992 Jun. 15; 148(12):4072-6.

Zhao Q, Temsamani J, Iadarola P L, Jiang Z, Agrawal S Effect of different chemically modified oligodeoxynucleotides on immune stimulation. Biochem Pharmacol 1996 Jan. 26; 51(2):173-82.

Zeuzem S, Feinman S V, Rasenack J, Heathcote E J, Lai M Y, Gane E, O'Grady J, Reichen J, Diago M, Lin A, Hoffman J, Brunda M J. Peginterferon alfa-2a in patients with chronic hepatitis C. N Engl J Med. 2000 Dec. 7; 343(23): 1666-72.

Zimmermann S, Egeter O, Hausmann S, Lipford G B, Rocken M, Wagner H, Heeg K. CpG oligodeoxynucleotides trigger protective and curative Th1 responses in lethal murine leishmaniasis. J Immunol. 1998 Apr. 15; 160(8):3627-30.

The invention claimed is:

1. A method for enhancing steroid efficacy in a steroid refractory patient afflicted with ulcerative colitis or Crohn's disease and currently on steroid anti-inflammatory treatment but not responding or responding poorly or inadequately to the steroid anti-inflammatory treatment, comprising administering to the patient an oligonucleotide having the sequence 5'-GGAACAGTTCGTCCATGGC-3' (SEQ ID NO: 1), wherein at least one CG dinucleotide is unmethylated, wherein the oligonucleotide is administered in an amount effective to improve sensitivity of the patient to the steroid anti-inflammatory treatment and thereby induce a clinical response to the steroid anti-inflammatory treatment.

2. The method according to claim 1, wherein said patient is currently on corticosteroid anti-inflammatory treatment.

3. The method according to claim 1, wherein said oligonucleotide comprises at least one modified sugar moiety nucleobase.

4. The method according to claim 3, wherein the modified sugar moiety is a 2'-O-methoxyethyl sugar moiety.

5. The method according to claim 1, wherein the amount of oligonucleotide administered to the patient is about 0.01 µg to about 100 mg per kg body weight.

6. The method according to claim 1, wherein the amount of oligonucleotide administered to the patient is about 0.1 µg to about 10 mg per kg body weight.

7. The method according to claim 1, wherein the amount of oligonucleotide administered to the patient is about 1 µg to about 5 mg per kg body weight.

8. The method according to claim 1, wherein the oligonucleotide is administered via inhalation, or opthalmically, intranasally, parenterally, orally, intradermally, or rectally.

9. The method according to claim 1, wherein the patient is human.

10. The method according to claim 1, wherein the patient is afflicted with ulcerative colitis.

11. The method according to claim 1, wherein the patient is afflicted with Crohn's disease.

12. The method according to claim 1, wherein said oligonucleotide comprises at least one nucleotide having a backbone modification.

13. The method according to claim 12, wherein said oligonucleotide comprises at least one nucleotide having a phosphate backbone modification.

14. The method according to claim 13, wherein the phosphate backbone modification is a phosphorothioate or phosphorodithioate modification.

15. The method according to claim 13, wherein the phosphate backbone modification is on the 5' inter-nucleotide linkages.

16. The method according to claim 13, wherein the phosphate backbone modification is on the 3' inter-nucleotide linkages.

17. The method according to claim 13, wherein the phosphate backbone modification is on the 5' inter-nucleotide linkages and the 3' inter-nucleotide linkages.

18. The method according to claim 12, wherein the modification occurs at one or more nucleotides at any position along the entire length of said oligonucleotide.

19. The method according to claim 1, wherein the oligonucleotide has the sequence 5'-G*G*A*ACAGTTCGTCCAT*G*G*C-3' (SEQ ID NO: 1), wherein at least one CG dinucleotide is unmethylated, and * indicates phosphorothioate linkage, with remaining linkages comprising phosphodiester linkages.

20. The method according to claim 2, wherein said patient is currently on corticosteroid anti-inflammatory treatment.

21. The method according to claim 2, wherein said oligonucleotide comprises at least one modified sugar moiety nucleobase.

22. The method according to claim 21, wherein the modified sugar moiety is a 2'-O-methoxyethyl sugar moiety.

23. The method according to claim 2, wherein the amount of oligonucleotide administered to the patient is about 0.01 µg to about 100 mg per kg body weight.

24. The method according to claim 2, wherein the amount of oligonucleotide administered to the patient is about 0.1 µg to about 10 mg per kg body weight.

25. The method according to claim 2, wherein the amount of oligonucleotide administered to the patient is about 1 µg to about 5 mg per kg body weight.

26. The method according to claim 2, wherein the oligonucleotide is administered via inhalation, or opthalmically, intranasally, parenterally, orally, intradermally, or rectally.

27. The method according to claim 2, wherein the patient is human.

28. The method according to claim 2, wherein the patient is afflicted with ulcerative colitis.

29. The method according to claim 2, wherein the patient is afflicted with Crohn's disease.

30. The method according to claim 2, wherein said oligonucleotide comprises at least one nucleotide having a backbone modification.

31. The method according to claim 30, wherein said oligonucleotide comprises at least one nucleotide having a phosphate backbone modification.

32. The method according to claim 31, wherein the phosphate backbone modification is a phosphorothioate or phosphorodithioate modification.

33. The method according to claim 31, wherein the phosphate backbone modification is on the 5' inter-nucleotide linkages.

34. The method according to claim 31, wherein the phosphate backbone modification is on the 3' inter-nucleotide linkages.

35. The method according to claim 31, wherein the phosphate backbone modification is on the 5' inter-nucleotide linkages and the 3' inter-nucleotide linkages.

36. The method according to claim 30, wherein the modification occurs at one or more nucleotides at any position along the entire length of said oligonucleotide.

37. The method according to claim 2, wherein the oligonucleotide has the sequence 5'-G*G*A*ACAGTTCGTCCAT*G*G*C-3' (SEQ ID NO: 1), wherein at least one CG dinucleotide is unmethylated, and * indicates phosphorothioate linkage, with remaining linkages comprising phosphodiester linkages.

38. The method according to claim 1, wherein a single administration of the oligonucleotide is made.

39. The method according to claim 2, wherein a single administration of the oligonucleotide is made.

* * * * *

UNITED STATES PATENT AND TRADEMARK OFFICE Certificate

Patent No. 8,258,107 B2                                                                 Patented: September 4, 2012

On petition requesting issuance of a certificate for correction of inventorship pursuant to 35 U.S.C. 256, it has been found that the above identified patent, through error and without any deceptive intent, improperly sets forth the inventorship.
Accordingly, it is hereby certified that the correct inventorship of this patent is: Robert Löfberg, Stockholm (SE); Oliver Von Stein, Upplands Väsby (SE); and Arezöu Zargari, Solna (SE).

Signed and Sealed this Twenty-first Day of May 2013.

HEATHER CALAMITA
*Supervisory Patent Examiner*
Art Unit 1635
Technology Center 1600